United States Patent
Komatsu et al.

(10) Patent No.: US 9,809,609 B2
(45) Date of Patent: *Nov. 7, 2017

(54) WATER-SOLUBLE BENZOAZEPINE COMPOUND AND ITS PHARMACEUTICAL COMPOSITION

(75) Inventors: Makoto Komatsu, Tokushima (JP); Fumitaka Goto, Tokushima (JP); Yasuhiro Menjo, Tokushima (JP); Keigo Yamada, Tokushima (JP); Takakuni Matsuda, Tokushima (JP); Yusuke Kato, Tokushima (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/461,642

(22) Filed: May 1, 2012

(65) Prior Publication Data

US 2012/0277188 A1    Nov. 1, 2012

Related U.S. Application Data

(63) Continuation of application No. 12/980,266, filed on Dec. 28, 2010, now abandoned, which is a continuation of application No. 12/159,027, filed as application No. PCT/JP2006/326311 on Dec. 22, 2006, now abandoned.

(30) Foreign Application Priority Data

Dec. 27, 2005 (JP) ................................. 2005-375457

(51) Int. Cl.
| | |
|---|---|
| C07F 9/553 | (2006.01) |
| A61K 31/675 | (2006.01) |
| A61P 9/08 | (2006.01) |
| A61P 9/12 | (2006.01) |
| A61P 7/02 | (2006.01) |
| A61P 7/00 | (2006.01) |

(52) U.S. Cl.
CPC ............. *C07F 9/5535* (2013.01); *Y02P 20/55* (2015.11)

(58) Field of Classification Search
CPC ..... C07D 223/16; C07D 405/12; A61K 31/55
See application file for complete search history.

(56) References Cited

U.S. PATENT DOCUMENTS

| | | | |
|---|---|---|---|
| 5,244,898 A | 9/1993 | Ogawa et al. | |
| 5,258,510 A | 11/1993 | Ogawa et al. | |
| 5,466,683 A * | 11/1995 | Sterling et al. | 514/80 |
| 5,753,677 A | 5/1998 | Ogawa et al. | |
| 5,972,882 A | 10/1999 | Gattone | |
| 6,436,989 B1 | 8/2002 | Hale et al. | |
| 6,838,474 B2 | 1/2005 | Tung et al. | |

FOREIGN PATENT DOCUMENTS

| | | |
|---|---|---|
| EP | 0 413 674 B1 | 2/1996 |
| JP | 11-021241 | 1/1999 |
| JP | 11021241 * | 1/1999 |
| WO | WO 97/28169 | 8/1997 |
| WO | WO 2004/073716 A1 | 9/2004 |

OTHER PUBLICATIONS

Prodrug_definition at http://medical-dictionary.thefree dictionary.com/prodrug.*
Rautio et al. in Nature Reviews 7, 255-269 (2008).*
Office Action in copending U.S. Appl. No. 13/461,665 dated Feb. 12, 2013.
Fleisher, D. et al, "Improved Oral Drug Delivery: Solubility Limitations Overcome by the Use of Prodrugs," *Adv. Drug Delivery Rev.* 19:115-30 (1996).
Gheorghiade, M. et al., "Vasopressin $V_2$ -Receptor Blockade With Tolvaptan in Patients With Chronic Heart Failure," *Circulation* 107:2690-96 (2008).
Medical Subject Headings, "Tolvaptan," entry dated Jan. 25, 1999; retrieved on Apr. 6, 2009, from http://www/nlm.nih.gov/egi/mesh/2009/MB_egi?mold=&term=tolvaptan.
Prodrug_definition at http://medical-dictionary.thefree dictionary.com/prodrug—May 26, 2011.
Yamamura, Y. et al., "OPC-41061, a Highly Potent Human Vasopressin $V_2$ -Receptor Antagonist: Pharmacological Profile and Aquaretic Effect by Single and Multiple Oral Dosing in Rats[1]," *J. Pharmacol. Exper. Therapeutics* 287:860-67 (1998).

(Continued)

*Primary Examiner* — Dennis Heyer
(74) *Attorney, Agent, or Firm* — Finnegan, Henderson, Farabow, Garrett & Dunner, LLP

(57) ABSTRACT

The present invention provides a benzoazepine compound represented by following general formula (1):

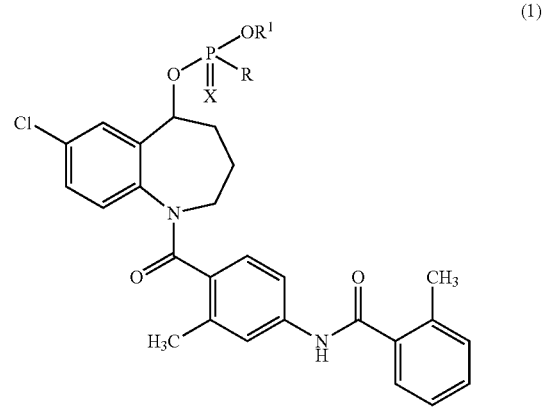

or a salt thereof,
wherein R represents a hydrogen atom, a hydroxy group optionally protected with a protecting group, etc., $R^1$ represents a hydrogen atom or hydroxy-protecting group, and X represents an oxygen atom or a sulfur atom. The benzoazepine compound of the present invention and salts thereof have high solubility in water, and can be suitably used for injections.

13 Claims, 2 Drawing Sheets

(56) References Cited

OTHER PUBLICATIONS

Office Action dated Aug. 24, 2009, of corresponding application in Singapore (Application No. 080415-6).
International Search Report dated Apr. 4, 2007, of application PCT/JP2006/326311.
Rautio, Jarkko et al., "Prodrugs: design and clinical applications," Nature Reviews 7, pp. 255-269 (2008).

* cited by examiner (n=4, mean ± S.D.)

WATER-SOLUBLE BENZOAZEPINE COMPOUND AND ITS PHARMACEUTICAL COMPOSITION

This is a continuation of application Ser. No. 12/980,266, filed Dec. 28, 2010, now abandoned which is a continuation of U.S. application Ser. No. 12/159,027, filed on Jun. 24, 2008 (now abandoned), which is a national stage application under 35 U.S.C. §371 of International Application No. PCT/JP2006/326311, filed on Dec. 22, 2006, which claims the benefit of priority to Japanese Application No. 2005-375457, filed on Dec. 27, 2005, all of which are incorporated herein by reference.

TECHNICAL FIELD

The present invention relates to a novel benzoazepine compound and its pharmaceutical composition.

BACKGROUND OF ART

Tolvaptan represented by the following formula (2) is a known compound, and has been disclosed in, for example, U.S. Pat. No. 5,258,510 specification (Example 1199).

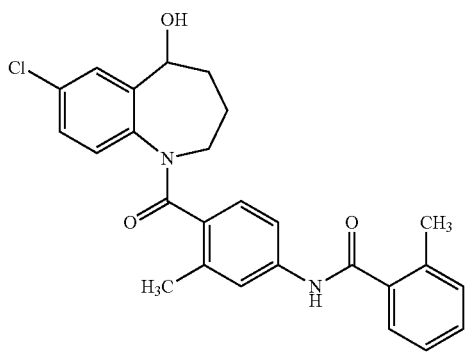

(2)

It is known that tolvaptan is useful as a vasopressin antagonist having aquaretic activity (Circulation, 107, pp. 2690-2696 (2003)). However, because of its low water solubility, tolvaptan has problems in that it is poorly absorbed by the intestinal canal, its dosage form and administration route are limited, etc. Although attempts have been made to solve these problems so that, for example, tolvaptan can be administered in the form of an amorphous solid preparation composition (Japanese Unexamined Patent Publication No. 1999-21241), in the application of tolvaptan, its dosage form and administration route still remain limited.

DISCLOSURE OF THE INVENTION

The present invention aims to provide a novel benzoazepine compound for improving the solubility of tolvaptan in water.

The present inventors conducted extensive research to solve the above problem, and as a result found that when tolvaptan is in the form of a phosphate ester compound, the water solubility thereof can be remarkably improved.

The present invention has been accomplished based on this finding.

Specifically, the present invention provides the following benzoazepine compounds, and compositions comprising the same, as described in Item 1 to 13 below.

Item 1. A benzoazepine compound represented by general formula (1)

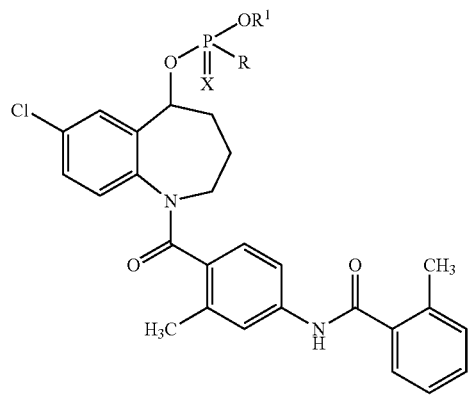

(1)

or a salt thereof,
wherein R represents a hydrogen atom, a hydroxy group optionally protected with a protecting group, a mercapto group optionally protected with a protecting group, or an amino group optionally protected with one or two protecting groups; $R^1$ represents a hydrogen atom or a hydroxy-protecting group; and X represents an oxygen atom or a sulfur atom.

Item 2. A benzoazepine compound according to item 1 or a salt thereof, wherein X is an oxygen atom.

Item 3. A benzoazepine compound according to item 1 or 2, or a salt thereof, wherein R is a hydroxy group optionally protected with a protecting group.

Item 4. A benzoazepine compound according to item 1 or 2, or a salt thereof, wherein R is a hydrogen atom, a mercapto group optionally protected with a protecting group, or an amino group optionally protected with one or two protecting groups.

Item 5. A benzoazepine compound according to any one of items 1, 2, 3 and 4, or a salt thereof, wherein $R^1$ is a hydroxy-protecting group.

Item 6. A benzoazepine compound according to any one of items 1, 2, 3 and 4, or a salt thereof, wherein $R^1$ is a hydrogen atom.

Item 7. A benzoazepine compound according to item 1 or a salt thereof, wherein X is a sulfur atom.

Item 8. A benzoazepine compound according to item 1 or a salt thereof, wherein X is an oxygen atom, R is a hydroxy group, and $R^1$ is a hydrogen atom.

Item 9. A pharmaceutical composition comprising a benzoazepine compound of item 1 or a pharmaceutically acceptable salt thereof, together with a pharmaceutically acceptable diluent and/or carrier.

Item 10. A pharmaceutical composition according to item 9, for use as a vasodilator, hypotensor, aquaretic agent, PKD, or platelet aggregation inhibitor.

Item 11. An aqueous solution composition comprising a benzoazepine compound of item 1 or a pharmaceutically acceptable salt thereof.

Item 12. An aqueous solution composition according to item 11, comprising a benzoazepine compound of item 1 or a pharmaceutically acceptable salt thereof, together with a buffer, isotonizing agent and injection solvent, and which is in the form of an injection.

Item 13. An aqueous solution composition according to item 12, further comprising a pH adjuster.

"Lower" as used herein indicates $C_{1-6}$ unless otherwise noted.

Examples of protecting groups for a "hydroxy group optionally protected with a protecting group", "mercapto group optionally protected with a protecting group" and "hydroxy-protecting group" include lower alkyl groups, phenyl(lower)alkyl groups, cyano lower alkyl groups, and lower alkyloxycarbonyl lower alkyl groups.

Examples of protecting groups for an "amino group optionally protected with one or two protecting groups" include lower alkyl groups optionally bearing hydroxy group(s).

Examples of lower alkyl groups and lower alkyl groups in phenyl(lower)alkyl groups, cyano lower alkyl groups, lower alkyloxycarbonyl lower alkyl groups, and lower alkyl groups optionally bearing hydroxy group(s) include $C_{1-6}$ straight or branched alkyl groups, for example, methyl, ethyl, n-propyl, isopropyl, n-butyl, isobutyl, tert-butyl, sec-butyl, n-pentyl, isopentyl, neopentyl, n-hexyl, isohexyl, 3-methylpentyl, and the like.

Preferable phenyl(lower)alkyl groups are, for example, benzyl, phenethyl, 3-phenylpropyl, trityl, etc.

Preferable cyano lower alkyl groups are $C_{1-6}$ straight or branched alkyl groups substituted with one to three cyano groups, for example, cyanomethyl, 2-cyanoethyl, 1-, 2-, or 3-cyano-n-propyl, 1-, 2-, or 3-cyano-isopropyl, 1-, 2-, 3-, or 4-cyano-n-butyl, 1-, 2-, 3-, or 4-cyano-isobutyl, 1-, 2-, 3-, or 4-cyano-tert-butyl, 1-, 2-, 3-, or 4-cyano-sec-butyl, 1-, 2-, 3-, 4-, or 5-cyano-n-pentyl, 1-, 2-, 3-, 4-, or 5-cyano-isopentyl, 1-, 2-, 3-, 4-, or 5-cyano-neopentyl, 1-, 2-, 3-, 4-, 5-, or 6-cyano-n-hexyl, 1-, 2-, 3-, 4-, 5-, or 6-cyano-isohexyl, 1-, 2-, 3-, 4-, 5-, or 6-cyano-3-methylpentyl, and the like.

Preferable lower alkyloxycarbonyl lower alkyl groups are alkyloxycarbonylalkyl groups wherein the alkyloxy moiety is a $C_{1-6}$ straight or branched alkyloxy group and the alkyl moiety is a $C_{1-6}$ straight or branched alkyl group, for example, methoxycarbonylmethyl, ethoxycarbonylmethyl, n-propoxycarbonylmethyl, isopropoxycarbonylmethyl, n-butoxycarbonylmethyl, isobutoxycarbonylmethyl, n-pentoxycarbonylmethyl, n-hexyloxycarbonylmethyl, 2-methoxycarbonylethyl, 3-methoxycarbonylpropyl, 4-methoxycarbonylbutyl, 5-methoxycarbonylpentyl, 6-methoxycarbonylhexyl, and the like.

Preferable lower alkyl groups optionally bearing hydroxy group(s) are $C_{1-6}$ straight or branched alkyl groups optionally substituted with one to three hydroxy groups, for example, methyl, ethyl, n-propyl, isopropyl, n-butyl, isobutyl, tert-butyl, sec-butyl, n-pentyl, isopentyl, neopentyl, n-hexyl, isohexyl, 3-methylpentyl, hydroxymethyl, 2-hydroxyethyl, 1-, 2-, or 3-hydroxy-n-propyl, 1-, 2-, or 3-hydroxy-isopropyl, 1-, 2-, 3-, or 4-hydroxy-n-butyl, 1-, 2-, 3-, or 4-hydroxy-isobutyl, 1-, 2-, 3-, or 4-hydroxy-tert-butyl, 1-, 2-, 3-, or 4-hydroxy-sec-butyl, 1-, 2-, 3-, 4-, or 5-hydroxy-n-pentyl, 1-, 2-, 3-, 4-, or 5-hydroxy-isopentyl, 1-, 2-, 3-, 4-, or 5-hydroxy-neopentyl, 1-, 2-, 3-, 4-, 5-, or 6-hydroxy-n-hexyl, 1-, 2-, 3-, 4-, 5-, or 6-hydroxy-isohexyl, 1-, 2-, 3-, 4-, 5-, or 6-hydroxy-3-methylpentyl, and the like.

Preferable amino groups optionally substituted with one or two protecting group(s) are amino groups optionally bearing one or two $C_{1-6}$ straight or branched alkyl groups optionally bearing one to three hydroxy groups, for example, amino, methylamino, dimethylamino, ethylamino, diethylamino, n-propylamino, di-n-propylamino, iso-propylamino, di-iso-propylamino, n-butyl amino, di-n-butylamino, iso-butyl amino, di-so-butylamino, tert-butyl amino, di-tert-butylamino, n-pentyl amino, di-n-pentylamino, n-hexyl amino, di-n-hexylamino, hydroxymethylamino, 2-hydroxyethylamino, diethylamino, di-(2-hydroxyethyl)amino, 3-hydroxypropylamino, 4-hydroxybutyl amino, and the like.

Among benzoazepine compounds represented by the above general formula (1), the following compounds and salts thereof are preferable:

when X is an oxygen atom, (1) compounds wherein R is a hydroxy group and $R^1$ is a hydrogen atom, (2) compounds wherein R is a hydroxy group and $R^1$ is a hydroxy-protecting group, (3) compounds wherein R is a mercapto group and $R^1$ is a hydroxy-protecting group, and (4) compounds wherein R is an amino group protected with one or two protecting groups, and $R^1$ is a hydroxy-protecting group; and when X is a sulfur atom, (1) compounds wherein R is an hydroxy group and $R^1$ is a hydrogen atom or hydroxy-protecting group.

Particularly preferable of these is the compound wherein X is an oxygen atom, R is a hydroxy group, and $R^1$ is a hydrogen atom; or a salt thereof.

Benzoazepine compounds represented by the above general formula (1) can be produced by various methods, and an example thereof is a method as shown by the following reaction schemes 1 to 7:

Reaction scheme-1

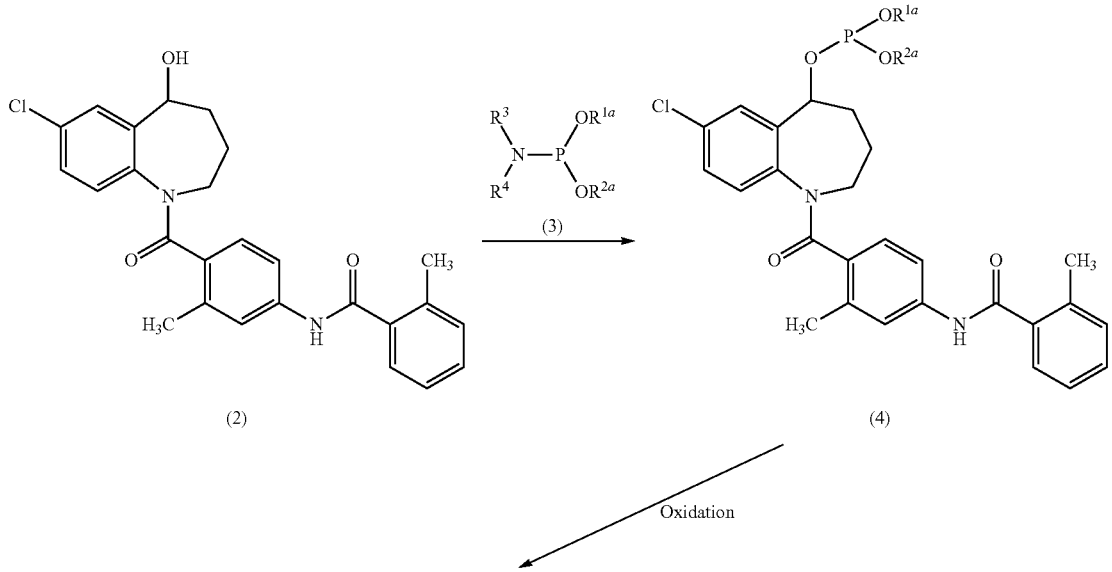

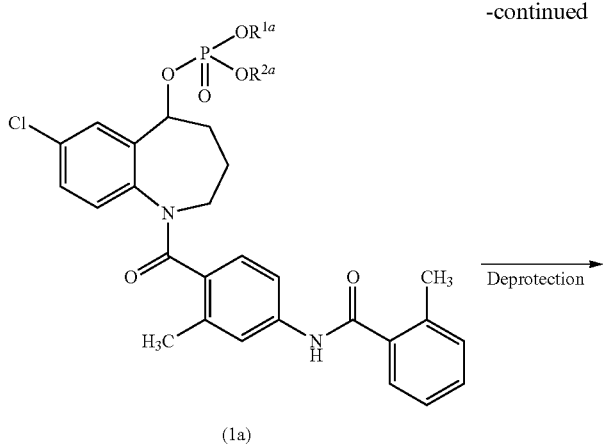

(1a)

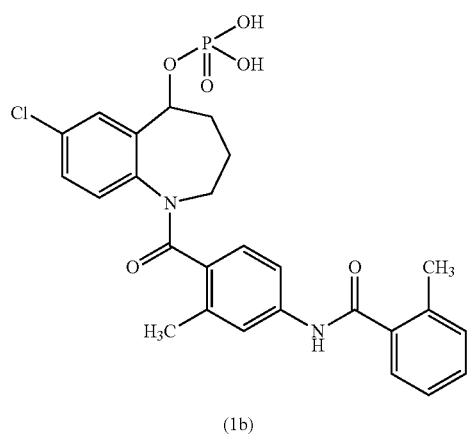

(1b)

wherein $R^3$ and $R^4$ are independently a lower alkyl group or optionally-substituted phenyl group, or $R^3$ and $R^4$ may instead be linked together through or without one or more additional heteroatoms to form, together with the nitrogen atom to which they are bound, a 5- to 8-membered saturated or unsaturated ring; and $R^{1a}$ and $R^{2a}$ may be the same or different, and each represents a hydroxy-protecting group.

Examples of lower alkyl groups are as mentioned above, including $C_{1-6}$ straight or branched alkyl groups, for example, methyl, ethyl, n-propyl, isopropyl, n-butyl, isobutyl, tert-butyl, sec-butyl, n-pentyl, isopentyl, neopentyl, n-hexyl, isohexyl, 3-methylpentyl, and the like.

Examples of substituents for optionally-substituted phenyl groups include lower alkyl groups as above; $C_{1-6}$ straight or branched alkoxy groups, for example, methoxy, ethoxy, propoxy, isopropoxy, butoxy, tert-butoxy, pentyloxy, hexyloxy, and the like; and halogen atoms, for example, fluorine, chlorine, bromine, iodine, and the like.

Preferable examples of optionally-substituted phenyl groups include phenyl; 2-, 3- or 4-methylphenyl; 2-, 3- or 4-chlorophenyl; 2-, 3-, or 4-methoxyphenyl; etc.

Examples of 5- to 8-membered saturated or unsaturated rings formed by $R^3$ and $R^4$ being linked together include morpholine ring, etc.

Compound (4) can be produced by reacting compound (2) with compound (3) in a suitable solvent in the presence of acid.

Examples of solvents include halogenated hydrocarbon solvents, for example, methylene chloride, chloroform, 1,2-dichloroethane, carbon tetrachloride, and the like; esters, for example, ethyl acetate and the like; aromatic hydrocarbons, for example, benzene, toluene, xylene, and the like; acetonitrile; etc.

Examples of acids include mild acids, for example, 1H-tetrazole, 5-methyltetrazole, pyridinium hydrobromide, and the like.

The amount of acid is usually at least about 1 mole, and preferably about 1 to about 10 moles, per mol of compound (2).

The amount of compound (3) is usually 0.5 to 2 moles, and preferably 0.7 to 1.5 moles, per mol of compound (2).

The reaction temperature is usually −20 to 50° C., preferably 0 to 50° C., and more preferably 0° C. to room temperature. The reaction time is usually 15 minutes to 24 hours, preferably 30 minutes to 6 hours, and more preferably 1 to 3 hours.

Compound (1a) can be produced by reacting compound (4) with an oxidizing agent in a suitable solvent.

Examples of solvents include halogenated hydrocarbon solvents, for example, methylene chloride, chloroform, 1,2-dichloroethane, carbon tetrachloride, and the like; esters, for example, ethyl acetate and the like; aromatic hydrocarbons, for example, benzene, toluene, xylene, and the like; acetonitrile; etc.

Examples of oxidizing agents include peracids, for example, hydrogen peroxide, and metachloroperbenzoic acid, peracetic acid, permaleic acid, and the like.

The amount of oxidizing agent is usually at least about 1 mole, and preferably about 1 to about 3 moles, per mol of compound (4).

The reaction temperature is usually −100 to 50° C., preferably −40° C. to room temperature, and more preferably −40 to 0° C. The reaction time is usually 15 minutes to 24 hours, preferably 30 minutes to 6 hours, and more preferably 30 minutes to 2 hours.

Compound (1b) can be obtained by deprotecting the protected hydroxy groups of compound (1a) by routine methods.

When, for example, the hydroxy-protecting groups are lower alkyl groups, deprotection can be performed under routine hydrolysis conditions.

Such hydrolysis is preferably performed in the presence of base or acid (including Lewis acid).

A wide range of known inorganic and organic bases can be used as such a base. Preferable inorganic bases are, for example, alkali metals (e.g., sodium, potassium, etc.); alkaline earth metals (e.g., magnesium, calcium, etc.); and their hydroxides, carbonates and hydrogencarbonates. Preferable organic bases are, for example, trialkylamines (e.g., trimethylamine, triethylamine, etc.), picoline, and 1,5-diazabicyclo[4,3,0]non-5-ene.

A wide range of known organic and inorganic acids can be used as such an acid. Preferable organic acids are fatty acids, for example, formic acid, acetic acid, propionic acid, and the like; and trihaloacetic acids, for example, trichloroacetic acid, trifluoroacetic acid, and the like. Preferable inorganic acids are, for example, hydrochloric acid, hydrobromic acid, sulfuric acid, hydrogen chloride, hydrogen bromide, etc. Examples of Lewis acids include boron trifluoride ether complex, boron tribromide, aluminium chloride, ferric chloride, etc.

When a trihaloacetic acid or Lewis acid is used, the hydrolysis is preferably performed in the presence of cation scavenger (e.g., anisole, phenol, etc).

The amount of base or acid is not limited so long as it satisfies hydrolysis requirements.

The reaction temperature is usually −20 to 100° C., preferably 0 to 50° C., and more preferably 0° C. to room temperature. The reaction time is usually 5 minutes to 24 hours, preferably 15 minutes to 6 hours, and more preferably 15 minutes to 3 hours.

When, for example, the hydroxy-protecting groups are phenyl(lower)alkyl groups, deprotection can be preformed by a routine catalytic reduction.

Catalysts suitable for such catalytic reduction are platinum catalysts (e.g., platinum plate, spongy platinum, platinum black, colloidal platinum, platinum oxide, platinum wire, etc.), palladium catalysts (e.g., spongy palladium, palladium black, palladium oxide, palladium carbon, palladium/barium sulfate, palladium/barium carbonate, etc.), nickel catalysts (e.g., reduced nickel, nickel oxide, Raney nickel, etc.), cobalt catalysts (e.g., reduced cobalt, Raney cobalt, etc.), iron catalysts (e.g., reduced iron, etc.), and the like. When a palladium carbon catalyst is used, the catalytic reduction is preferably performed in the presence of zinc bromide.

The amount of catalyst used for the catalytic reduction is not limited, and may be a routine amount.

The reaction temperature is usually 0 to 100° C., preferably 0 to 50° C., and more preferably room temperature to 50° C. The reaction time is usually 5 minutes to 24 hours, preferably 5 minutes to 3 hours, and more preferably 5 minutes to 1 hour.

Reaction scheme-2

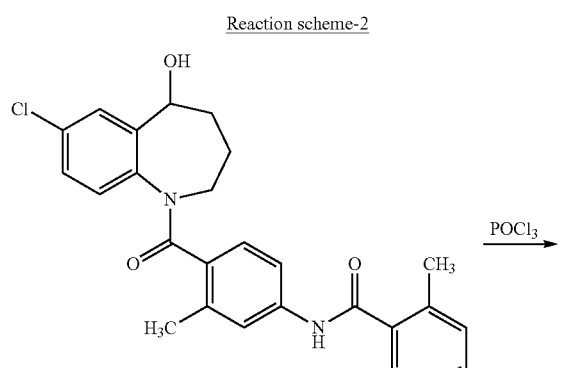

Compound (2) is reacted with phosphorus oxychloride, and then hydrolyzed to give compound (1b).

The amount of phosphorus oxychloride is usually 1 mole to large excess, and preferably 1 to 5 moles, per mol of compound (2).

The above reaction is carried out in the presence of basic compound in a suitable solvent.

Examples of solvents for the reaction with phosphorus oxychloride include ethers, for example, diethyl ether, dioxane, tetrahydrofuran, monoglyme, diglyme, and the like; halogenated hydrocarbon solvents, for example, methylene chloride, chloroform, 1,2-dichloroethane, carbon tetrachloride, and the like; esters, for example, ethyl acetate and the like; aromatic hydrocarbons, for example, benzene, toluene, xylene, and the like; acetonitrile; etc.

Examples of basic compounds include carbonates, for example, sodium carbonate, potassium carbonate, sodium bicarbonate, potassium bicarbonate, cesium carbonate, and the like; alkali metal hydroxides, for example, sodium hydroxide, potassium hydroxide, and the like; alkali earth metal hydroxides, for example, calcium hydroxide and the like; phosphates, for example, potassium phosphate, sodium phosphate, and the like; organic bases, for example, pyridine, imidazole, N-ethyldiisopropylamine, dimethylaminopyridine, triethylamine, trimethylamine, dimethylaniline, N-methylmorpholine, 1,5-diazabicyclo[4.3.0]non-5-ene (DBN), 1,8-diazabicyclo[5.4.0]undec-7-ene (DBU), 1,4-diazabicyclo[2.2.2]octane (DABCO), and the like; and mixtures thereof.

The amount of basic compound is usually at least about 3 moles, and preferably about 3 to about 10 moles, per mol of compound (2). The reaction temperature is usually −100 to 50° C., preferably −50° C. to room temperature, and more preferably −30° C. to room temperature. The reaction time is usually 15 minutes to 24 hours, preferably 30 minutes to 6 hours, and more preferably 1 to 3 hours.

Hydrolysis can be achieved by adding water to the above reaction mixture or adding the reaction mixture to water.

Because this is usually accompanied by excess reagent decomposition and heat is thereby generated, hydrolysis is preferably carried out with cooling. To complete the reaction, heating is preferably carried out after the initial reaction has subsided.

The reaction time is usually 15 minutes to 24 hours, preferably 30 minutes to 6 hours, and more preferably 1 to 3 hours.

Reaction scheme-3

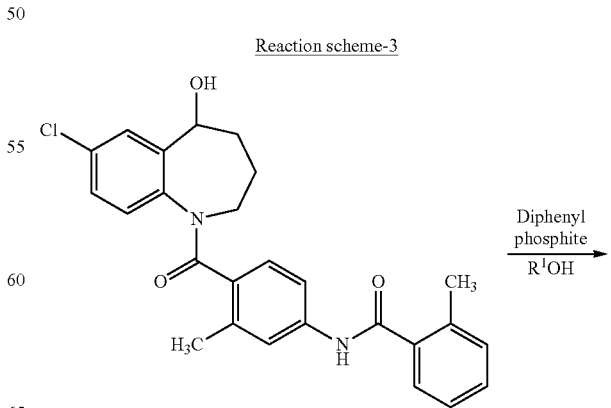

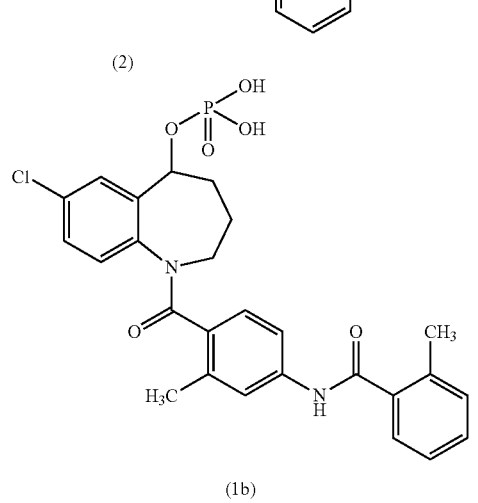

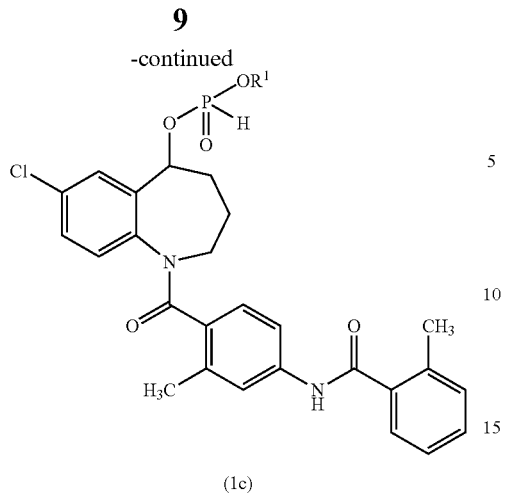

(1c)

wherein R¹ is the same as above.

Compound (2) is reacted with diphenyl phosphite, and then reacted with an alcohol (R¹OH) to give compound (1c).

The amount of diphenyl phosphite is usually 1 mole to large excess, and preferably 1 to 5 moles, per mol of compound (2). The amount of alcohol ($R^{10}H$) is usually 1 mole to large excess, and preferably 1 to 10 moles, per mol of compound (2).

The above reaction is carried out in the presence of basic compound in a suitable solvent.

Examples of solvents include ethers, for example, diethyl ether, dioxane, tetrahydrofuran, monoglyme, diglyme, and the like; halogenated hydrocarbon solvents, for example, methylene chloride, chloroform, 1,2-dichloroethane, carbon tetrachloride, and the like; esters, for example, ethyl acetate and the like; aromatic hydrocarbons, for example, benzene, toluene, xylene, and the like; and acetonitrile.

Examples of basic compounds include carbonates, for example, sodium carbonate, potassium carbonate, sodium bicarbonate, potassium bicarbonate, caesium carbonate, and the like; alkali metal hydroxides, for example, sodium hydroxide, potassium hydroxide, and the like; alkali earth metal hydroxides, for example, calcium hydroxide and the like; phosphates, for example, potassium phosphate, sodium phosphate, and the like; organic bases, for example, pyridine, imidazole, N-ethyldiisopropylamine, dimethylaminopyridine, triethylamine, trimethylamine, dimethylaniline, N-methylmorpholine, 1,5-diazabicyclo[4.3.0]non-5-ene (DBN), 1,8-diazabicyclo[5.4.0]undec-7-ene (DBU), 1,4-diazabicyclo[2.2.2]octane (DABCO), and the like; and mixtures thereof.

The amount of basic compound is usually at least about 1 mole, and preferably about 1 to about 10 moles, per mol of compound (2). Organic solvents may also be used as solvent.

The reaction temperature is usually −100 to 50° C., preferably −50° C. to room temperature, and more preferably −30° C. to room temperature. The reaction time is usually 15 minutes to 24 hours, preferably 30 minutes to 6 hours, and more preferably 1 to 3 hours.

Reaction scheme-4

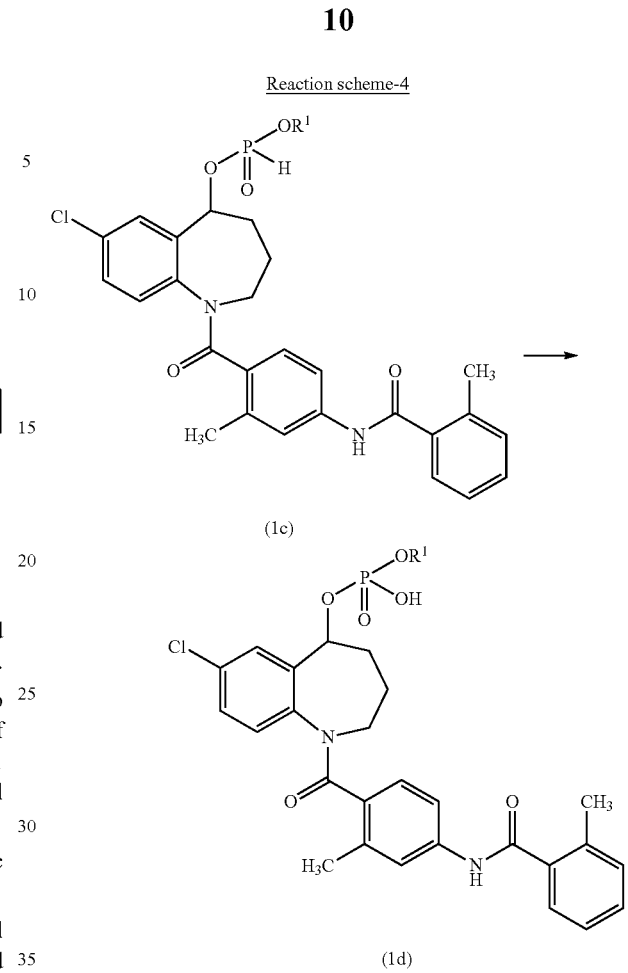

wherein R¹ is the same as above.

Oxidization of phosphite can be carried out using about 1 to about 3 equivalents of phosphorous acid-oxidizing agent, at a temperature in the range of about 0° C. to about 50° C. Preferably, the reaction is carried out using about 5 to about 15% excess phosphorous acid-oxidizing agent at 0° C. to room temperature.

A phosphorous acid-oxidizing agent is a reagent that oxidizes a phosphite to a phosphate. Examples thereof include peroxides, for example, hydrogen peroxide; metachloroperbenzoic acid and the like; iodine in water; bromine; nitrogen tetroxide; etc. Iodine in water is preferable.

The above reaction is carried out in a suitable solvent.

Examples of solvents include ethers, for example, diethyl ether, dioxane, tetrahydrofuran, monoglyme, diglyme, and the like; halogenated hydrocarbon solvents, for example, methylene chloride, chloroform, 1,2-dichloroethane, and the like; esters, for example, ethyl acetate and the like; aromatic hydrocarbons, for example, benzene, toluene, xylene, and the like; acetonitrile; and pyridine.

The reaction temperature is usually −100 to 50° C., preferably −50° C. to room temperature, and more preferably −30° C. to room temperature. The reaction time is usually 15 minutes to 24 hours, preferably 15 minutes to 6 hours, and more preferably 15 minutes to 3 hours.

Reaction scheme-5

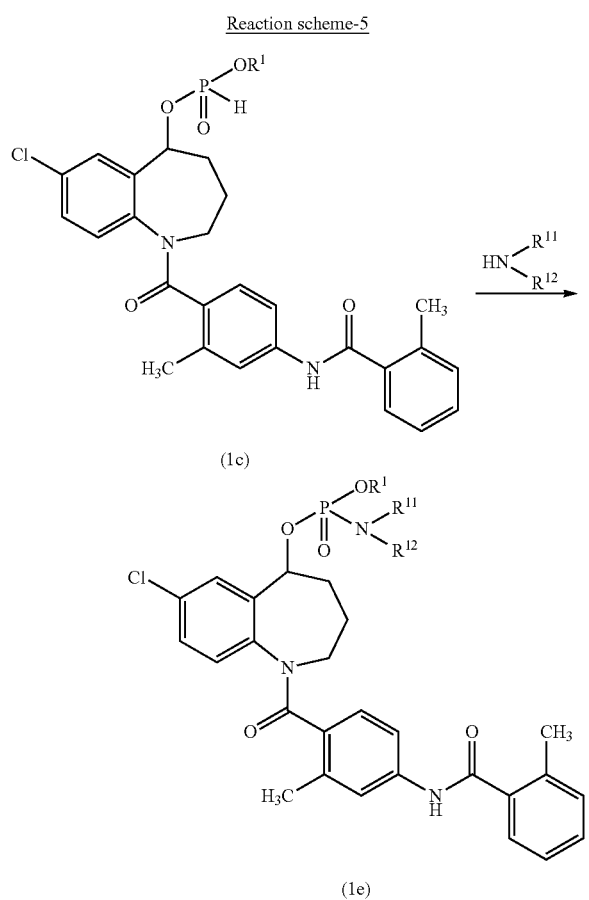

wherein $R^1$ is the same as above; and $R^{11}$ and $R^{12}$ may the same or different, and each represents a hydrogen atom or a lower alkyl group optionally bearing hydroxy group(s).

Amine ($R^{11}R^{12}NH$) and carbon tetrachloride are reacted with phosphorous acid diester (1c) to give phosphoroamidite (1e).

Sodium hypochlorite may also be used in place of carbon tetrachloride.

The amount of carbon tetrachloride is usually 1 mole to large excess, and preferably 1 to 5 moles, per mol of compound (1c). The amount of amine ($R^{11}R^{12}NH$) is usually 1 mole to large excess, and preferably 1 to 10 moles, per mol of compound (1c).

The above reaction is carried out in the presence of basic compound in a suitable solvent.

Examples of solvents include ethers, for example, diethyl ether, dioxane, tetrahydrofuran, monoglyme, diglyme, and the like; halogenated hydrocarbon solvents, for example, methylene chloride, chloroform, 1,2-dichloroethane, carbon tetrachloride, and the like; esters, for example, ethyl acetate, and the like; aromatic hydrocarbons, for example, benzene, toluene, xylene, and the like; acetonitrile; etc.

Examples of basic compounds include carbonates, for example, sodium carbonate, potassium carbonate, sodium bicarbonate, potassium bicarbonate, caesium carbonate, and the like; alkali metal hydroxides, for example, sodium hydroxide, potassium hydroxide, and the like; alkali earth metal hydroxides, for example, calcium hydroxide and the like; phosphates, for example, potassium phosphate, sodium phosphate, and the like; organic bases, for example, pyridine, imidazole, N-ethyldiisopropylamine, dimethylaminopyridine, triethylamine, trimethylamine, dimethylaniline, N-methylmorpholine, 1,5-diazabicyclo[4.3.0]non-5-ene (DBN), 1,8-diazabicyclo[5.4.0]undec-7-ene (DBU), 1,4-diazabicyclo[2.2.2]octane (DABCO), and the like; and mixtures thereof. The amount of basic compound is usually at least about 1 mole, and preferably about 1 to 10 about moles, per mol of compound (2). Organic solvents may also be used as solvent.

The reaction temperature is usually −100 to 50° C., preferably −50° C. to room temperature, and more preferably −30° C. to room temperature. The reaction time is usually 1 minute to 24 hours, preferably 1 minute to 6 hours, and more preferably 1 minute to 3 hours.

Reaction scheme-6

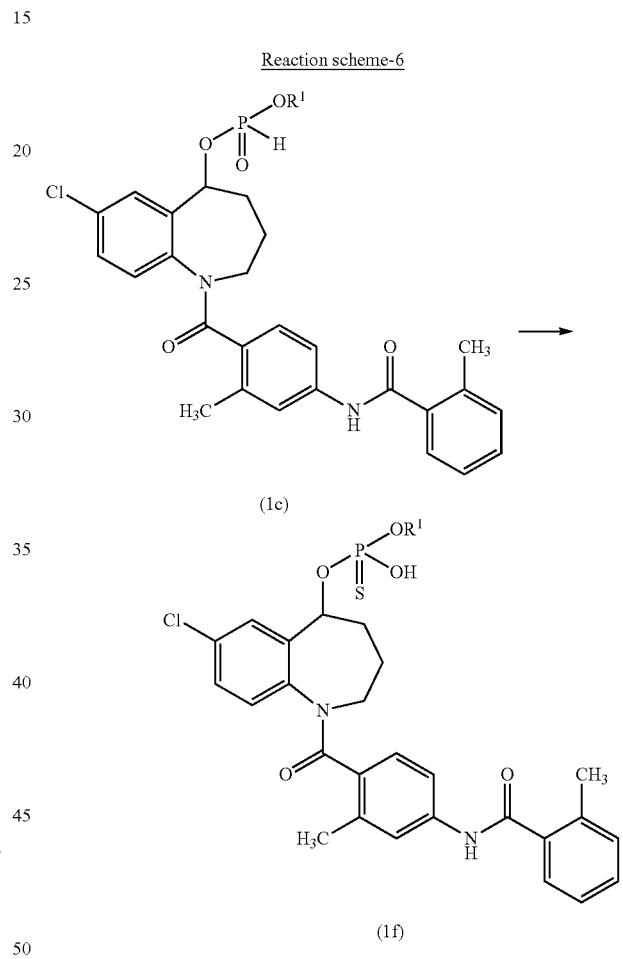

wherein $R^1$ is the same as above.

Phosphorous acid diester (1c) is reacted with sulfur to give phosphorothioic acid diester (1f).

The amount of sulfur usually 1 mole to large excess, and preferably 1 to 5 moles, per mol of compound (1c).

The above reaction is carried out in the presence of basic compound in a suitable solvent.

Examples of solvents include ethers, for example, diethyl ether, dioxane, tetrahydrofuran, monoglyme, diglyme, and the like; halogenated hydrocarbon solvents, for example, methylene chloride, chloroform, 1,2-dichloroethane, and the like; esters, for example, ethyl acetate and the like; aromatic hydrocarbons, for example, benzene, toluene, xylene, and the like; acetonitrile; and pyridine.

Examples of basic compounds include carbonates, for example, sodium carbonate, potassium carbonate, sodium bicarbonate, potassium bicarbonate, caesium carbonate, and the like; alkali metal hydroxides, for example, sodium hydroxide, potassium hydroxide, and the like; alkali earth metal hydroxides, for example, calcium hydroxide and the like; phosphates, for example, potassium phosphate, sodium phosphate, and the like; alkali metal hydrides, for example, sodium hydride, potassium hydride, and the like; alkali metals, for example, potassium, sodium, and the like; sodium amide; metal alcoholates, for example, sodium methylate, sodium ethylate, sodium n-butoxide, sodium tert-butoxide, potassium tert-butoxide, and the like; organic bases, for example, pyridine, imidazole, N-ethyldiisopropylamine, dimethylaminopyridine, triethylamine, trimethylamine, dimethylaniline, N-methylmorpholine, 1,5-diazabicyclo[4.3.0]non-5-ene (DBN), 1,8-diazabicyclo[5.4.0]undec-7-ene (DBU), 1,4-diazabicyclo[2.2.2]octane (DABCO), and the like; and mixtures thereof. The amount of basic compound is usually at least about 1 mole, and preferably about 1 to about 10 moles, per mol of compound (2). Organic solvents may also be used as solvent.

The reaction temperature is usually −100 to 50° C., preferably −50° C. to room temperature, and more preferably −30° C. to room temperature. The reaction time is usually 15 minutes to 24 hours, preferably 30 minutes to 6 hours, and more preferably 1 to 3 hours.

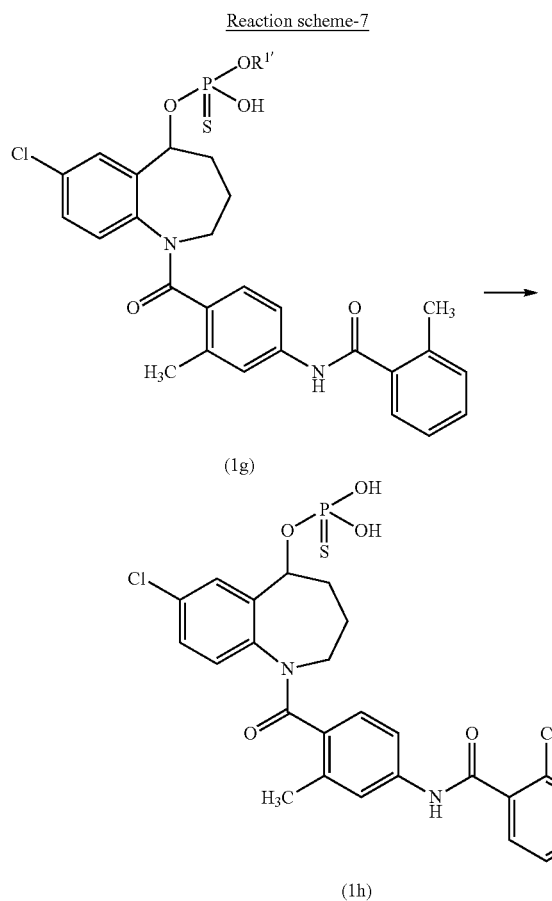

wherein $R^{1'}$ is a hydroxy-protecting group.

The protecting group of compound (1g), which is a compound (1f) obtained by reaction scheme 6 wherein $R^1$ is a hydroxy-protecting group, is removed to give compound (1 h).

When $R^1$ is a cyanoethyl group, the protecting group can be removed by using a basic compound.

The above reaction is carried out in the presence of basic compound in a suitable solvent.

Examples of solvents include water; alcohols, for example, methanol, ethanol, isopropyl alcohol, and the like; ethers, for example, diethyl ether, dioxane, tetrahydrofuran, monoglyme, diglyme, and the like; halogenated hydrocarbon solvents, for example, methylene chloride, chloroform, 1,2-dichloroethane, carbon tetrachloride, and the like; esters, for example, ethyl acetate and the like; aromatic hydrocarbons, for example, benzene, toluene, xylene, and the like; aprotic polar solvents, for example, dimethylformamide (DMF), dimethylsulfoxide (DMSO), and the like; ketones, for example, acetone, methyl ethyl ketone, methyl isobutyl ketone, and the like; acetonitrile; and mixtures thereof.

Examples of basic compounds include carbonates, for example, sodium carbonate, potassium carbonate, sodium bicarbonate, potassium bicarbonate, caesium carbonate, and the like; alkali metal hydroxides, for example, sodium hydroxide, potassium hydroxide, and the like; alkali earth metal hydroxides, for example, calcium hydroxide and the like; phosphates, for example, potassium phosphate, sodium phosphate, and the like; alkali metal hydrides, for example, sodium hydride, potassium hydride, and the like; alkali metals, for example, potassium, sodium, and the like; sodium amide; metal alcoholates, for example, sodium methylate, sodium ethylate, sodium n-butoxide, sodium tert-butoxide, potassium tert-butoxide, and the like; organic bases, for example, pyridine, imidazole, N-ethyldiisopropylamine, dimethylaminopyridine, triethylamine, trimethylamine, dimethylaniline, N-methylmorpholine, 1,5-diazabicyclo[4.3.0]non-5-ene (DBN), 1,8-diazabicyclo[5.4.0]undec-7-ene (DBU), 1,4-diazabicyclo[2.2.2]octane (DABCO), and the like; and mixtures thereof. The amount of basic compound is usually at least about 1 mole, and preferably about 1 to about 10 moles, per mol of compound (2). Organic solvents may also be used as solvent.

The reaction temperature is usually −100 to 50° C., preferably −50° C. to room temperature, and more preferably −30° C. to room temperature. The reaction time is usually 15 minutes to 24 hours, preferably 30 minutes to 6 hours, and more preferably 1 to 3 hours.

Compounds (2), (3), (4), (1a), (1b), (1c), (1d), (1e), (1f), (1g) and (1 h) in the above reaction schemes may be suitable salts thereof. Examples of such suitable salts include the same kinds of salts as with compound (1).

Compounds obtained according to the above reaction schemes can be isolated and purified from the reaction mixture by conventional manners, for example, after cooling the reaction mixture, isolating crude reaction product by filtration, concentration, extraction or like isolation procedure, and then purifying the resultant by column chromatography, recrystallization or like routine purification procedure.

Compounds represented by general formula (1) of the present invention include stereoisomers, optical isomers, and solvates (hydrates, ethanolates, etc.) thereof.

Examples of salts of compounds represented by general formula (1) of the present invention include pharmaceutically acceptable salts for example, metal salts, for example, alkali metal salts (e.g., sodium salts, potassium salts, etc.), alkaline earth metal salts (e.g., calcium salts, magnesium salts, etc.) and the like; ammonium salts; organic base salts (e.g., trimethylamine salts, triethylamine salts, pyridine salts, picoline salts, dicyclohexylamine salts, ethylenediamine salts, N,N'-dibenzylethylenediamine salts, tris(hydroxymethyl)aminomethane salts, ethanolamine salts, etc.); etc. Among these, alkali metal salts are preferable, and sodium salts are more preferable.

Such salts can be easily formed by applying, to the compound of the present invention, the corresponding pharmaceutically acceptable basic compound. Examples of applicable basic compounds include sodium hydroxide, potassium hydroxide, calcium hydroxide, sodium carbonate, potassium hydrogencarbonate, etc.

The compound of the present invention has, for example, vasopressin antagonism, vasodilating activity, hypotensive activity, activity for inhibiting saccharide release in liver, mesangial cell growth inhibitory activity, aquaretic activity, and platelet aggregation inhibitory activity. The compound is useful as a vasodilator, hypotensor, aquaretic agent and platelet aggregation inhibitor, and is effective in the prevention and treatment of hypertension, edema (e.g., cardiac edema, hepatic edema, renal edema, cerebral edema), abdominal dropsy, heart failure (e.g., severe heart failure), renal dysfunction, syndrome of inappropriate secretion of vasopressin (SIADH), liver cirrhosis, hyponatremia, hypokalemia, diabetes, circulatory insufficiency, polycystic kidney disease (PKD), cerebral infarction, myocardial infarction, and the like.

When administered to the human body as a medicine, the compound of the present invention may be used simultaneously or separately with other vasopressin antagonists, ACE inhibitors, β-blocking agents, aquaretic agents, angiotensin II antagonists (ARB), digoxin, and/or like pharmaceutical drugs.

The compound of the present invention is usually used in the form of a general pharmaceutical composition. Such a pharmaceutical composition can be prepared by a conventional method using diluents and/or excipients which are commonly used, for example, fillers, expanders, binders, moisturizers, disintegrators, surfactants, lubricants, etc.

The form of the pharmaceutical composition containing the compound of the present invention can be suitably selected depending on the purpose of the treatment. It may be in the form of, for example, a tablet, pill, powder, solution, suspension, emulsion, capsule, suppository, ointment, or granules. An aqueous solution composition, for example, injection, instillation, and the like is particularly preferable.

When, for example, preparing an injection by using the compound of the present invention, such an injection is preferably formulated into a solution, emulsion, or suspension that has been sterilized and is isotonic with blood. For preparing such a solution, emulsion or suspension using the compound of the present invention, any diluents commonly employed in this field may be used. Examples of such diluents include water, aqueous lactic acid solutions, ethyl alcohol, propylene glycol, ethoxylated isostearyl alcohol, polyoxylated isostearyl alcohol, and polyoxyethylene sorbitan fatty acid esters. Further, in this case, sodium chloride, glucose, mannitol, glycerol and the like isotonizing agents in amounts sufficient to prepare an isotonic solution may be mixed in the pharmaceutical composition. Ordinary pH adjusters, solubilizers, buffers, soothing agents and the like may also be added.

An injection containing the compound of the present invention can be prepared by a conventional method, using a compound represented by general formula (1) or pharmaceutically acceptable salt thereof, together with a buffer, isotonizing agent, injection solvent, and, if necessary, pH adjuster.

Examples of buffers include carbonates, borates, phosphates, citrates, tris(hydroxymethyl)aminomethane, malates, and tartrates. It is also possible to singly use an acid or base forming such a buffer.

Examples of pH adjusters include basic compounds, for example, sodium hydroxide and the like; acids, for example, hydrochloric acid and the like.

Further, colorants, preservatives, fragrances, flavorings, sweeteners, and the like, as well as other medicines, can also be mixed in the pharmaceutical composition, as necessary.

The content of the compound represented by general formula (1) of the present invention or a salt thereof in the pharmaceutical composition is not limited, and can be suitably selected from a wide range. The content is usually 0.01 to 70 wt % of the pharmaceutical composition.

The method for administering such a pharmaceutical composition is not limited, and it may be administered by a suitable method depending on the form of the pharmaceutical composition; the patient's age, gender, etc.; the degree of the patient's symptoms; and the like. For example, tablets, pills, solutions, suspensions, emulsions, granules and capsules may be orally administered. Injections may be administered by intravenous injection, alone or as a mixture with glucose, amino acid and/or like ordinary replenishers. Injections may also be given alone by intramuscular, intracutaneous, subcutaneous or intraperitoneal administration, as necessary.

The dose of the pharmaceutical composition of the present invention can be selected depending on the usage; the patient's age, gender, etc.; the degree of the disease; and the like. The dose is usually such that the compound represented by general formula (1), which is an effective ingredient, is administered in an amount of 0.001 to 100 mg, and preferably 0.001 to 50 mg, per 1 kg of body weight per day in one or more administrations.

The dose varies with various conditions. A dose smaller than the above range may be sufficient, while a dose larger than the above range may be necessary.

The patents, patent applications, and documents cited herein are incorporated by reference.

Effect of the Invention

Compound (1) of the present invention or a salt thereof has remarkably excellent water solubility, excellent absorbability, etc.

Compound (1b) in particular or a salt thereof has remarkably excellent water solubility, excellent absorbability, etc.

When administered into the human body, compound (1) of the present invention or a salt thereof, compound (1b) or a salt thereof in particular, enables the easy generation of the active ingredient tolvaptan.

Further, compound (1) of the present invention or a salt thereof can be easily crystallized and is excellent in operability. In addition, compound (1) of the present invention or a salt thereof has excellent chemical stability.

Compound (1a) of the present invention can be suitably used as a starting material for producing compound (1b).

Use of compound (1) of the present invention or a salt thereof enables compositions to be provided in various forms that express drug efficacy equal to tolvaptan, which is an effective drug.

BEST MODE FOR CARRYING OUT THE INVENTION

Figure 1:
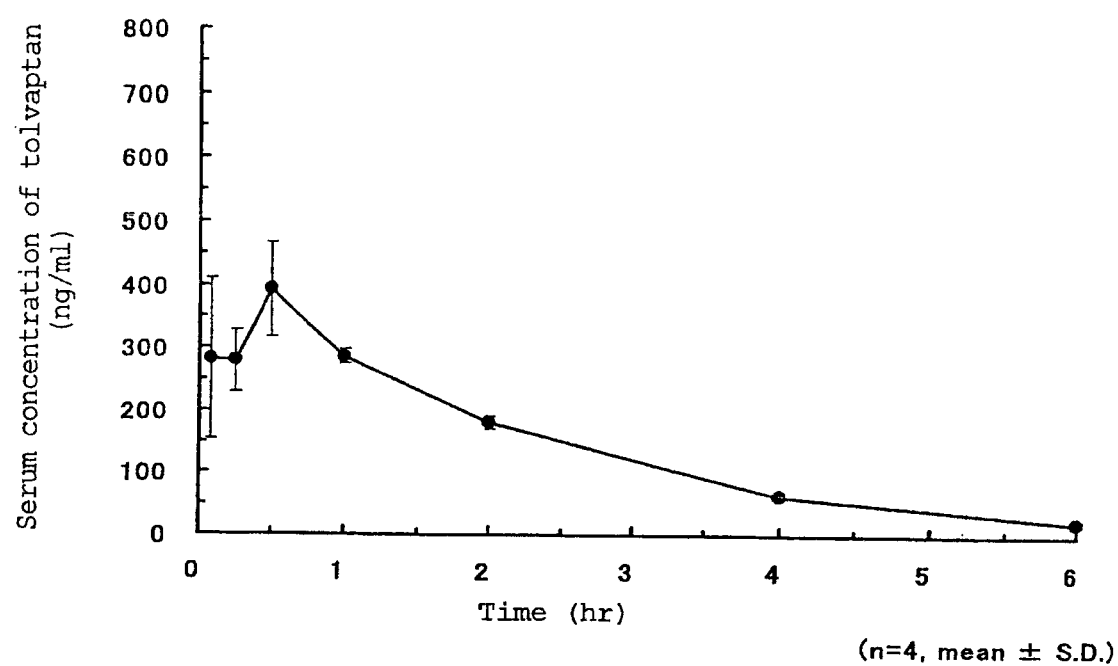
FIG. 1 is a graph showing the change in serum concentration of tolvaptan in female rats after rapid tail-vein administration of a solution of compound (1b) at a dose such that 1 mg of tolvaptan is produced per kg of body weight.

Examples, test examples and preparation examples are given below to illustrate the present invention in further detail, but the scope of the invention is not limited to these examples.

Example 1

A 1.0 g quantity of tolvaptan (compound (2)) and 460 mg of 1H-tetrazole were dissolved in 30 ml of methylene chloride, and 1.2 g of dibenzyl diisopropylphosphoramidite was added dropwise to this solution at room temperature with stirring. The mixture was then stirred for 2 hours at the same temperature.

The obtained reaction mixture was cooled to −40° C., and 6 ml of methylene chloride solution of 920 mg of metachloroperbenzoic acid was added dropwise thereto. The mixture was then stirred at the same temperature for 30 minutes, and at 0° C. for 30 minutes. The reaction mixture was washed with an aqueous sodium thiosulfate solution and saturated aqueous sodium bicarbonate, and then dried over anhydrous sodium sulfate. The obtained reaction mixture was filtered and concentrated, and the residue was purified by silica gel column chromatography (eluent: n-hexane:ethyl acetate=1:1) to give 1.5 g of amorphous compound (1a-1) (yield 97.2%).

NMR (DMSO-$d_6$, 100° C.) δ ppm; 9.86 (1H, br s), 7.56 (1H, s), 7.50-7.10 (17H, m), 7.00-6.80 (2H, m), 5.60-5.50 (1H, m), 5.15-5.00 (4H, m), 5.00-2.75 (2H, m), 2.36 (3H, s), 2.34 (3H, s), 2.10-1.70 (4H, m)

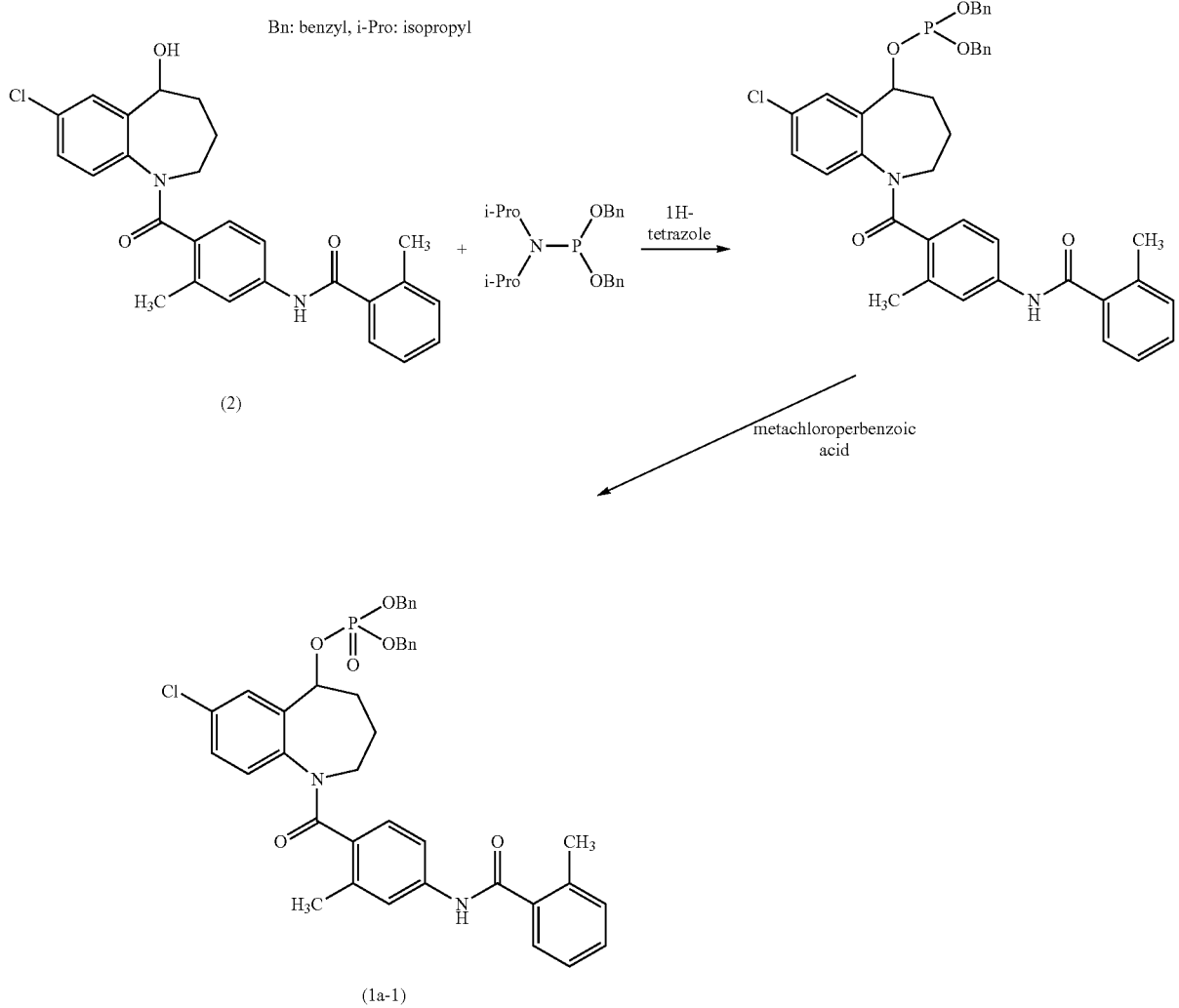

Example 2

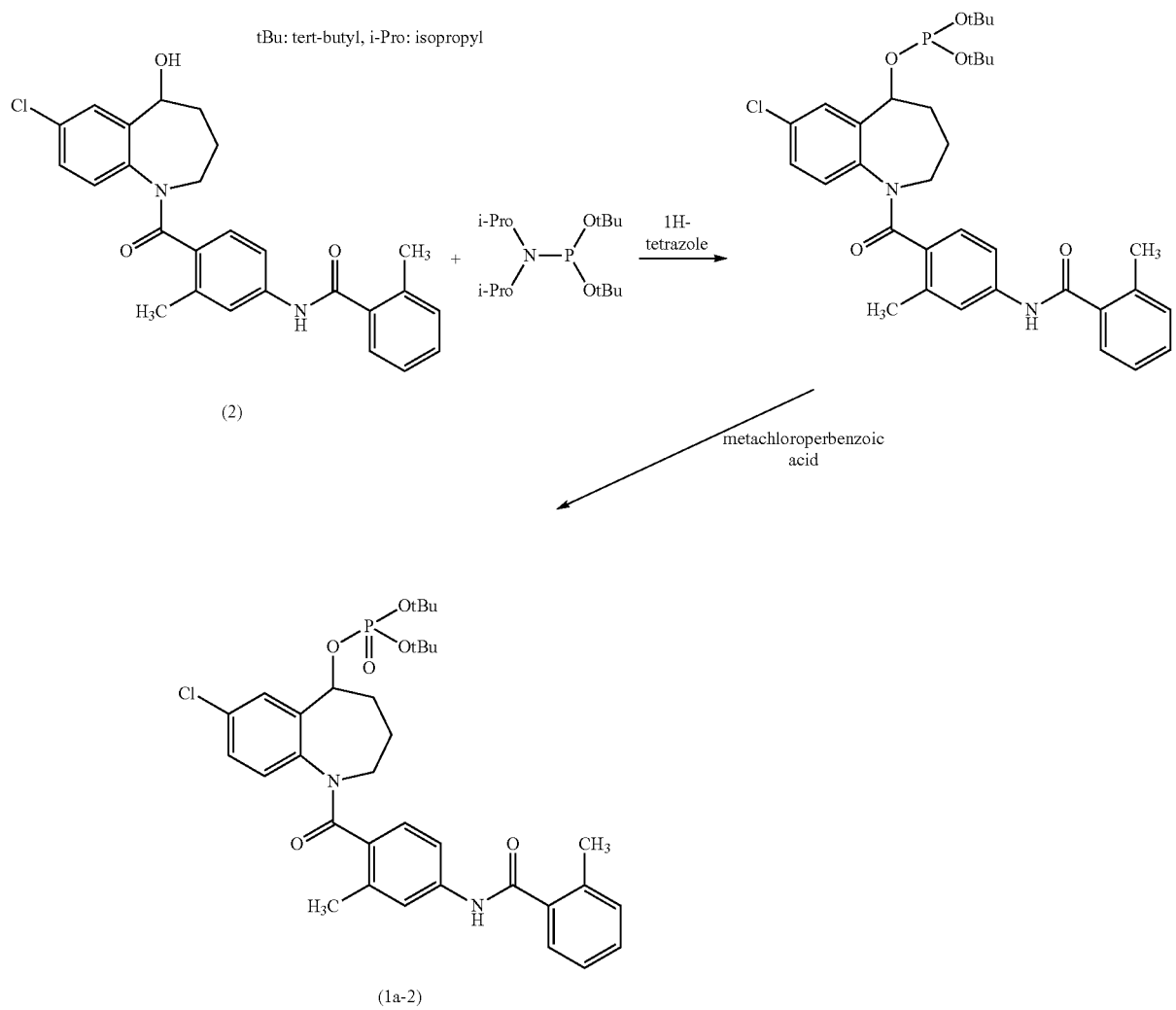

A 4.5 g quantity of tolvaptan (compound (2)) and 2.2 g of 1H-tetrazole were dissolved in 120 ml of methylene chloride, and a solution of 4.0 g of di t-butyl diisopropylphosphoramidite dissolved in 10 ml of methylene chloride was added dropwise to this solution with ice-cooling and stirring. The mixture was then stirred at room temperature for 2 hours.

The obtained reaction mixture was cooled to −40° C., and 20 ml of methylene chloride solution of 4.0 g of metachloro perbenzoic acid was added dropwise thereto. The mixture was then stirred at the same temperature for 30 minutes, and at 0° C. for 40 minutes. The reaction mixture was washed with an aqueous sodium thiosulfate solution and saturated aqueous sodium bicarbonate, and then dried over anhydrous sodium sulfate. The obtained reaction mixture was filtered and concentrated, and the residue was purified by silica gel column chromatography (eluent: hexane:ethyl acetate=1:1) to give 3.0 g of amorphous compound (1a-2) (yield 46.7%).

NMR (DMSO-$d_6$) δ ppm; 10.50-10.20 (1H, m), 8.00-6.50 (10H, m), 5.55-5.20 (1H, m), 4.90-4.50 (1H, m), 2.85-2.60 (1H, m), 2.40-2.20 (6H, m), 2.20-1.60 (4H, m), 1.60-1.30 (18H, m)

Example 3

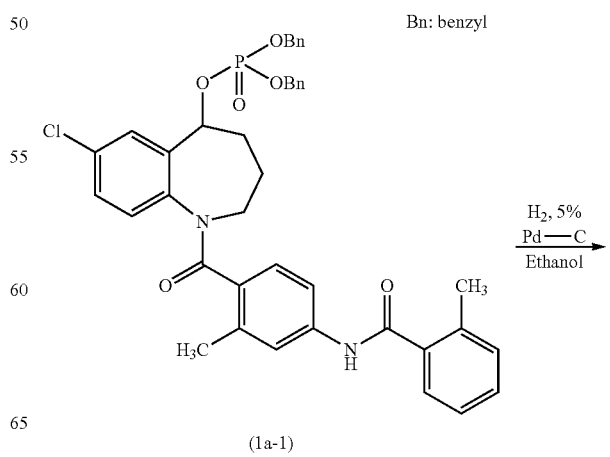

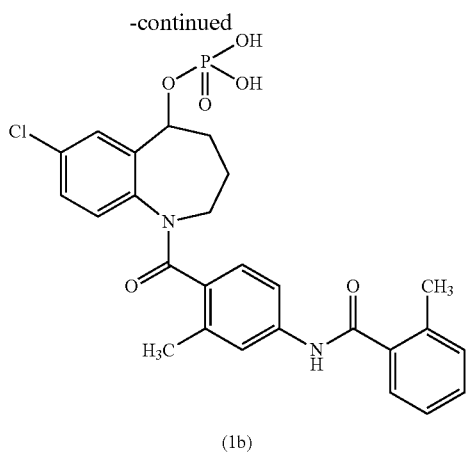

(1b)

A 5.3 g quantity of compound (1a-1) was dissolved in 100 ml of ethanol, and, using 2 g of 5% palladium-carbon as a catalyst, the solution was subjected to catalytic reduction at room temperature and atmospheric pressure for 10 minutes. The catalyst was removed from the solution by filtration, and the obtained filtrate was concentrated (4.2 g). The obtained residue was crystallized from methanol/water. The crystals were collected by filtration and then dried under reduced pressure (diphosphorus pentoxide) to give 3.5 g of white powdery compound (1b) (yield 88.5%).

Melting point: 150 to 152° C.

NMR (DMSO-$d_6$-$D_2O$, 100° C.) δ ppm; 7.50-6.70 (10H, m), 5.50-5.40 (1H, m), 5.00-2.50 (2H, m), 2.37 (6H, s), 2.40-1.50 (4H, m)

Example 4 tBu: tert-butyl

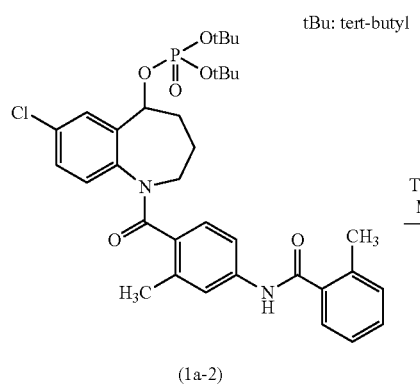

(1a-2)

Trifluoroacetic acid
Methylene cloride
→

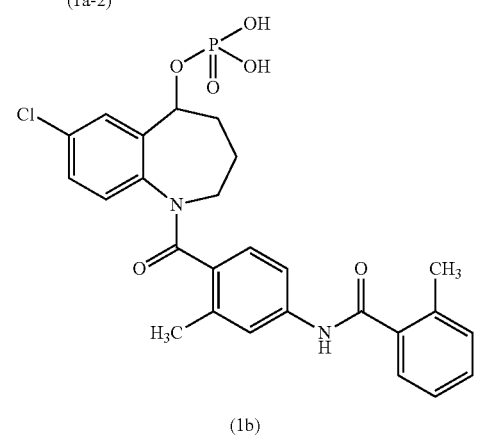

(1b)

A 3.0 g quantity of compound (1a-2) was dissolved in 100 ml of methylene chloride, and a solution of 10 ml of trifluoroacetic acid dissolved in 5 ml of methylene chloride was added dropwise to this solution with ice-cooling and stirring. The mixture was then stirred at the same temperature for 2 hours. The solvent was removed from the solution. The obtained residue was redissolved in methylene chloride, and then concentrated. The obtained residue was crystallized from methanol/water. The crystals were collected by filtration and then dried under reduced pressure (diphosphorus pentoxide) to give 1.9 g of white powdery compound (1b) (yield 76.8%).

Example 5

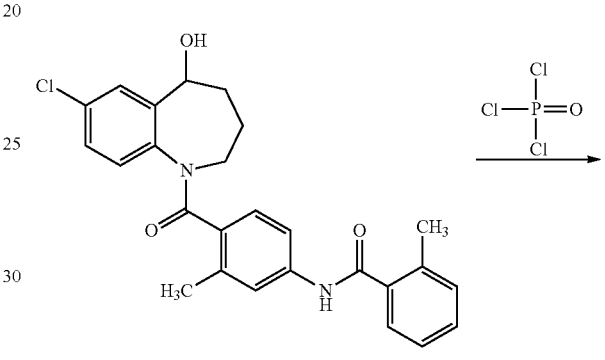

(2)

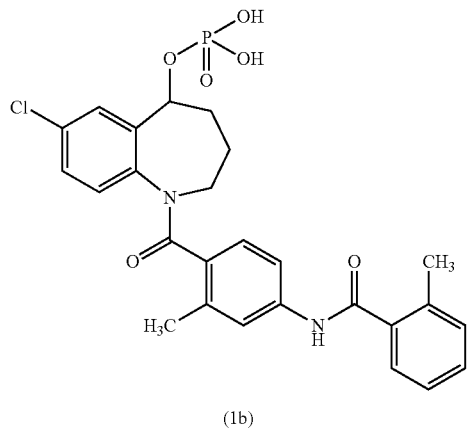

(1b)

A 240 ml quantity of 1,2-dimethoxyethane (DME) and 84 ml of triethylamine (0.60 mol, 9 equivalents) were added to 30 g (66 mmol) of tolvaptan (compound (2)), and the mixture was cooled under a nitrogen stream to −15° C. A 19 ml quantity (0.20 mol, 3 equivalents) of phosphorus oxychloride ($POCl_3$) was added dropwise to the obtained mixture at an internal temperature of no more than −12° C., and stirring was performed at −12° C. for 2 hours. A 200 ml quantity of 5 N sodium hydroxide aqueous solution was added to 1 kg of crashed ice, and the above reaction mixture were added in small portions thereto with stirring. To the obtained mixture was added 500 ml of toluene. The mixture was heated to 50° C. and then separated into an aqueous layer and a toluene layer. A 500 ml quantity of toluene was added again to the aqueous layer, stirring was performed at 50° C., and the mixture was then separated into an aqueous layer and a toluene layer. The aqueous layer was cooled to 10° C., 80 ml of 6 N hydrochloric acid was added thereto, and extraction was performed with 500 ml of ethyl acetate twice. The extract was dried over sodium sulfate and filtered, and the filtrate was concentrated. The concentrate was dried under reduced pressure at room temperature to give 34 g of amorphous compound (1b).

Yield: 97%

Example 6

Production of Calcium Salt of Compound (1b)

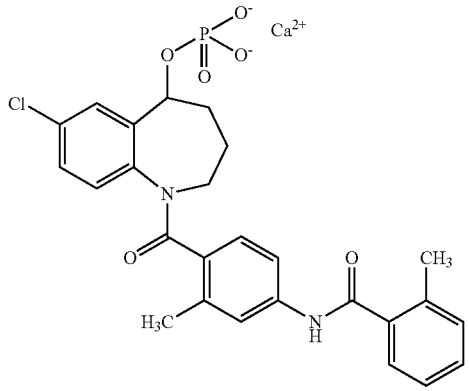 [SMILES: Cc1ccccc1C(=O)Nc1ccc(C(=O)N2CCCC(OP(=O)([O-])[O-])c3cc(Cl)ccc32)c(C)c1 ; [Ca+2]]

(1) A 2.6 g quantity (5.0 mmol) of compound (1b) was dissolved in 25 ml of isopropyl alcohol, and 2.2 ml of 5 N sodium hydroxide aqueous solution was added thereto at room temperature. The obtained mixture was concentrated under reduced pressure. To the residue was added 30 ml of water to dissolve the solid content, and an aqueous solution of 0.61 g (5.5 mmol) of calcium chloride was then added thereto. The precipitated solids were collected by filtration, washed with water, and hot air-dried at 60° C. to give 2.2 g of white powdery calcium salt of compound (1b).

Yield: 78%

$^1$H-NMR (DMSO-$d_6$, 100° C.) δ ppm: 1.3-2.4 (10H, m), 2.8-4.5 (2H, m), 5.2-5.8 (1H, m), 6.4-8.1 (10H, m), 9.0-10.2 (1H, m)

(2) A 280 mg quantity (0.53 mmol) of compound (1b) was dissolved in a mixed solution of 2 ml of methanol and 1 ml of water, and 43 mg (0.58 mmol) of calcium hydroxide was then added thereto. The mixture was stirred at room temperature for 1 hour. The precipitated solids were collected by filtration. The filtered material was suspended in methanol, stirred with heating, and then hot-filtered. The filtrate was concentrated, and the residue was recrystallized from methanol to give 75.4 mg of white powdery calcium salt of compound (1b).

Yield: 25%

Melting point: 263 to 265° C.

Example 7

Production of Magnesium Salt of Compound (1b)

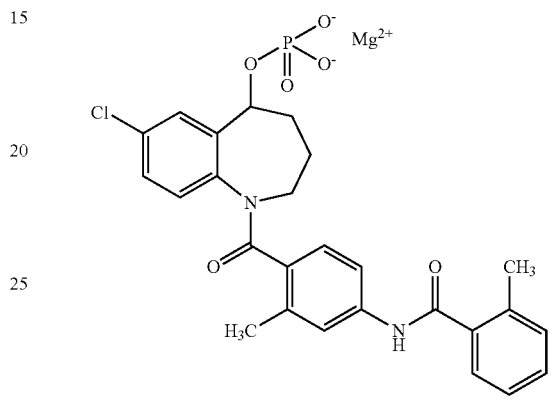

(1) A 1.0 g quantity (1.9 mmol) of compound (1b) was dissolved in 15 ml of methanol, and 0.76 ml of 5 N sodium hydroxide aqueous solution was added thereto. The mixture was concentrated under reduced pressure. The residue was dissolved in 10 ml of methanol, and 3 ml of methanol solution of 0.18 g of magnesium chloride was added to the obtained solution at room temperature. Precipitated insoluble matter (NaCl) was removed by filtration, and the filtrate was concentrated. To the residue was added 10 ml of water, and stirring was performed with heating. The mixture after stirring was allowed to cool to room temperature. The insoluble matter was then collected by filtration, washed with water, and dried under reduced pressure at 60° C. to give 400 mg of white powdery magnesium salt of compound (1b)

Yield: 38%

$^1$H-NMR (DMSO-$d_6$, 100° C.) δ ppm: 1.4-2.4 (10H, m), 2.8-4.5 (2H, m), 5.3-5.5 (1H, m), 6.4-7.8 (10H, m), 9.7 (1H, br).

(2) A 282 mg quantity (0.53 mmol) of compound (1b) was dissolved in 2 ml of methanol, and 41 mg (0.70 mmol) of magnesium ethoxide was added thereto with ice-cooling. To the obtained mixture were further added 2 ml of ethanol and an aqueous suspension (0.5 ml) of 36 mg (0.58 mmol) of magnesium hydroxide, and stirring was performed at room temperature for 1 hour. The insoluble matter was removed by filtration, and the filtrate was allowed to stand overnight. The precipitated solids were collected by filtration and then dried under reduced pressure to give 24.9 mg of white powdery magnesium salt of compound (1b).

Yield: 11%

Melting point: 250 to 252° C.

Example 8

Production of Monosodium Salt of Compound (1b)

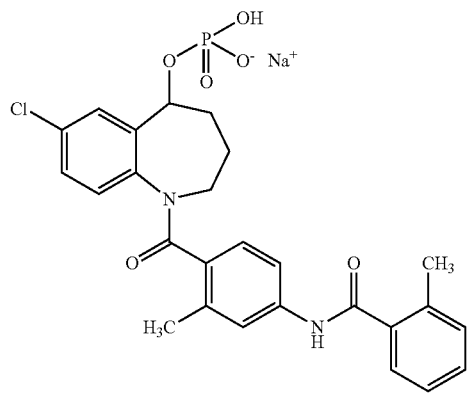 [SMILES: Cc1ccccc1C(=O)Nc1ccc(C(=O)N2CCCC(OP(=O)([O-])O)c3cc(Cl)ccc32)c(C)c1 ; [Na+]]

A 0.5 ml quantity of 1 N sodium hydroxide aqueous solution and 1 ml of water were added to a methanol solution (2 ml) of 266 mg (0.5 mmol) of compound (1b) with ice-cooling, and the obtained solution was stirred at room temperature for 1 hour. The reaction mixture was concentrated under reduced pressure, and the residue was recrystallized from methanol-water to give 45.2 mg of white powdery monosodium salt of compound (1b).

Yield: 16%

Melting point: 235 to 238° C.

Example 9

Production of Disodium Salt of a Compound (1b)

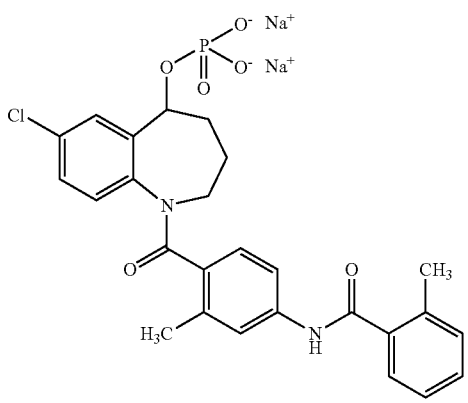 [SMILES: [Na+] ; Cc1ccccc1C(=O)Nc1ccc(C(=O)N2CCCC(OP(=O)([O-])[O-])c3cc(Cl)ccc32)c(C)c1 ; [Na+]]

A 1.0 ml quantity of 1 N sodium hydroxide aqueous solution was added to a methanol solution (2 ml) of 276 mg (0.52 mmol) of compound (1b) with ice-cooling, and the obtained mixture was stirred for 5 minutes. The reaction mixture was concentrated under reduced pressure, and the residue was recrystallized from acetone-water to give 221 mg of white powdery disodium salt of compound (1b).

Yield: 73%

Melting point: 250 to 252° C.

Example 10

Production of Diammonium Salt of Compound (1b)

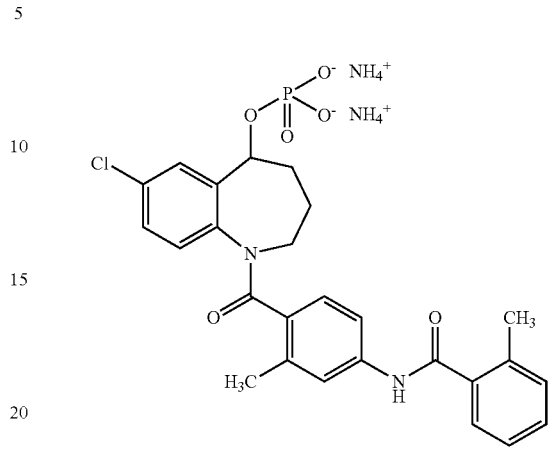

A 1.0 ml quantity of 25% aqueous ammonia solution was added to a methanol solution (2 ml) of 271 mg (0.51 mmol) of compound (1b) with ice-cooling, and the obtained mixture was stirred for 10 minutes. The reaction mixture was concentrated under reduced pressure, and the residue was recrystallized from methanol-water to give 104 mg of white powdery diammonium salt of compound (1b).

Yield: 36%.

Melting point: 195 to 198° C.

Example 11

Production of Monopotassium Salt of Compound (1b)

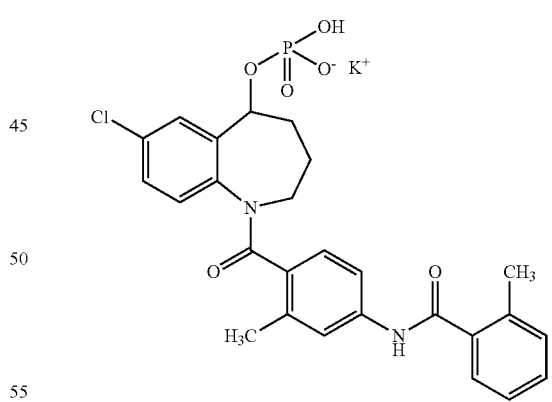

A 0.5 ml quantity of 1 N potassium hydroxide aqueous solution was added to a methanol solution (2 ml) of 276 mg (0.52 mmol) of compound (1b) with ice-cooling, and the obtained mixture was stirred for 10 minutes. The reaction mixture was concentrated under reduced pressure, and the residue was recrystallized from isopropyl alcohol to give 110.6 mg of white powdery monopotassium salt of compound (1b).

Yield: 37%

Melting point: 200 to 203° C.

Example 12

Production of Dipotassium Salt of Compound (1b)

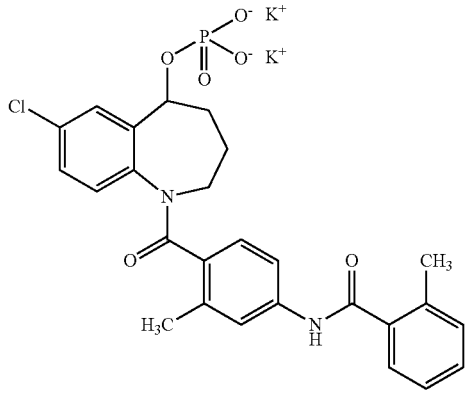 [SMILES: [K+] ; Cc1ccccc1C(=O)Nc1ccc(C(=O)N2CCCC(OP(=O)([O-])[O-])c3cc(Cl)ccc32)c(C)c1 ; [K+]]

A 1.0 ml quantity of 1 N potassium hydroxide aqueous solution was added to a methanol solution (2 ml) of 276 mg (0.52 mmol) of compound (1b) with ice-cooling, and the obtained mixture was stirred for 5 minutes. The reaction mixture was concentrated under reduced pressure, and diethyl ether was added to the residue. The insoluble matter was collected by filtration and then dried to give 273.9 mg of white powdery dipotassium salt of compound (1b).

Yield: 86%

Melting point: 255 to 265° C. (decomposition)

Example 13

Production of Zinc Salt of Compound (1b)

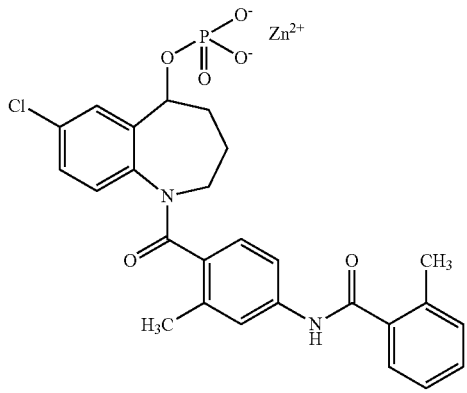 [SMILES: Cc1ccccc1C(=O)Nc1ccc(C(=O)N2CCCC(OP(=O)([O-])[O-])c3cc(Cl)ccc32)c(C)c1 ; [Zn+2]]

A 1.0 g quantity (1.9 mmol) of compound (1b) was dissolved in 15 ml of methanol, and 0.76 ml of 5 N sodium hydroxide aqueous solution was added to this solution. The mixture was concentrated under reduced pressure. The obtained residue was dissolved in 10 ml of methanol, and 3 ml of methanol solution of 259 mg of zinc chloride was added thereto at room temperature. Precipitated insoluble matter (NaCl) was removed by filtration, and the filtrate was concentrated. To the obtained residue was added 10 ml of water, and stirring was performed with heating. The mixture was then allowed to cool to room temperature. The insoluble matter was collected by filtration, washed with water, and dried under reduced pressure at 60° C. to give 900 mg of white powdery zinc salt of compound (1b).

Yield: 80%

Melting point: 235 to 239° C. (decomposition)

$^1$H-NMR (DMSO-$d_6$, 100° C.) δ ppm: 1.3-2.4 (10H, m), 2.8-4.5 (2H, m), 5.3-5.7 (1H, m), 6.6-7.7 (10H, m), 9.7 (1H, br)

Example 14

Production of Ethylenediamine Salt of Compound (1b)

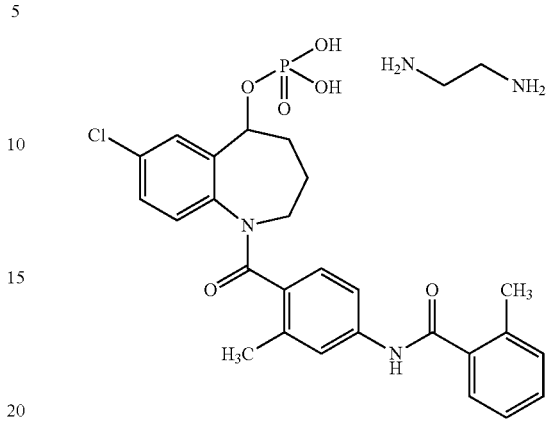

A 0.074 ml quantity (1.1 mmol) of ethylenediamine was added to an ethanol solution (10 ml) of 600 mg (1.1 mmol) of compound (1b). The obtained reaction mixture was concentrated under reduced pressure, and the residue was recrystallized from isoporpyl alcohol to give 250 mg of white powdery ethylenediamine salt of compound (1b).

$^1$H-NMR (DMSO-$d_6$, 100° C.) δ ppm: 1.5-2.0 (3H, m), 2.1-2.4 (7H, m), 2.77 (4H, s), 2.8-4.3 (2H, m), 5.3-5.5 (1H, m), 6.6-6.9 (1H, m), 6.9-7.2 (2H, m), 7.2-7.5 (5H, m), 7.58 (2H, d, J=7.6 Hz), 9.80 (1H, br)

Example 15

Production of Diethanolamine Salt of Compound (1b)

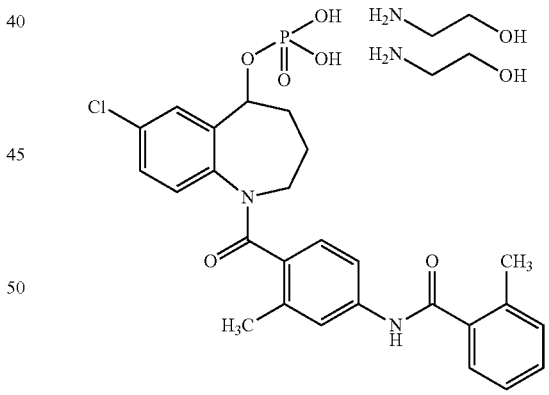

A 0.14 ml quantity (2.3 mmol) of ethanolamine was added to an isopropyl alcohol solution (6 ml) of 600 mg (1.1 mmol) of compound (1b). A 6 ml quantity of isopropyl alcohol was added to the obtained mixture, dissolution was performed with heating, and recrystallization from isopropyl alcohol gave 280 mg of white powdery diethanolamine salt of compound (1b).

$^1$H-NMR (DMSO-$d_6$, 100° C.) δ ppm: 1.4-2.0 (3H, R), 2.2-2.5 (7H, m), 2.75 (4H, t, J=5.5 Hz), 3.52 (4H, t, J=5.5 Hz), 2.8-4.3 (2H, m), 5.3-5.5 (1H, m), 6.7-6.9 (1H, m), 6.9-7.2 (2H, m), 7.2-7.4 (4H, m), 7.42 (1H, d, J=7.7 Hz), 7.57 (2H, d, J=6.5 Hz), 7.58 (2H, d, J=7.6 Hz), 9.80 (1H, br)

Example 16

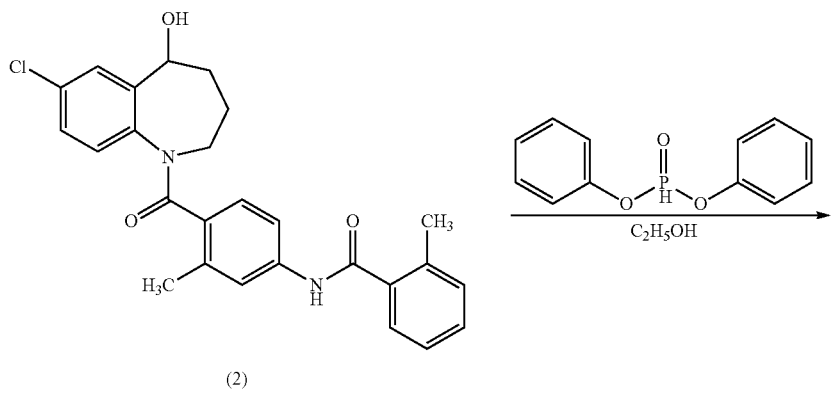

(2)

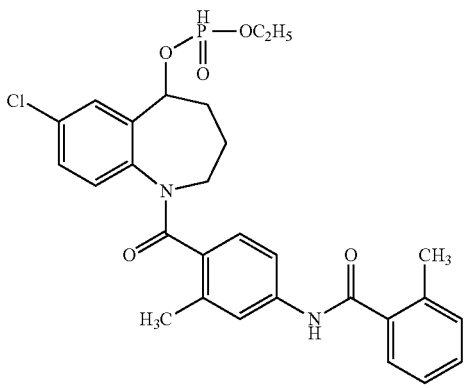

A 1.3 ml quantity (6.6 mmol) of diphenyl phosphite was added to a pyridine solution (10 ml) of 1.0 g (2.2 mmol) of tolvaptan (compound (2)) with ice-cooling. The obtained mixture was stirred at 0° C. for 30 minutes, and then at room temperature for 30 minutes. To the reaction mixture was added 0.58 ml of ethanol, and stirring was performed at room temperature for 30 minutes. To this mixture was added 1 N hydrochloric acid, and extraction was performed with ethyl acetate. The ethyl acetate layer was washed with a saturated aqueous sodium hydrogen carbonate solution, dried over sodium sulfate, and then filtered, and the filtrate was concentrated. The obtained residue was purified by silica gel column chromatography (n-hexane:ethyl acetate=27:73→0:100). The purified product was concentrated under reduced pressure, and the residue was dissolved in a mixed solvent of 10 ml of acetonitrile and 10 ml of water and then freeze-dried to give 450 mg of white amorphous solid target compound.

Yield: 38%

$^1$H-NMR (Toluene-$d_8$, 100° C.) δ ppm: 1.0-1.1 (3H, m), 1.4-1.9 (4H, m), 2.31 (3H, s), 2.42 (3H, s), 2.0-4.0 (2H, m), 3.7-4.1 (2H, m), 5.5 (0.5H, d, J=4.8 Hz), 6.4-7.5 (10H, m), 7.8 (0.5H, d, J=8.6 Hz)

Example 17

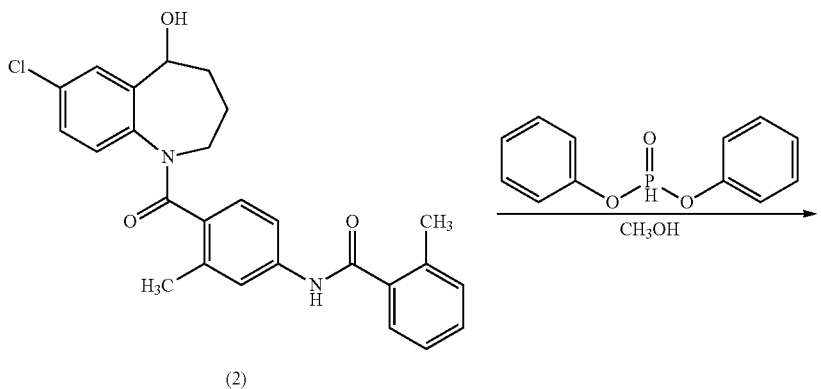

(2)

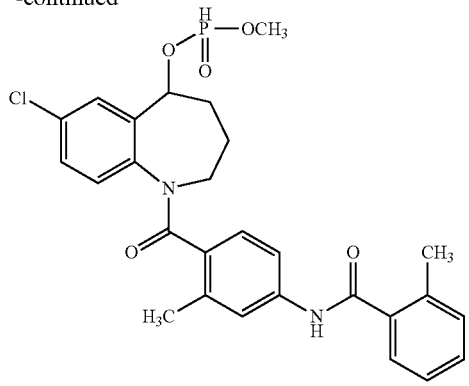

A pyridine solution (50 ml) of 10.0 g (22 mmol) of tolvaptan (compound (2)) was ice-cooled, and 13 ml (66 mmol) of diphenyl phosphite was slowly added thereto under a nitrogen atmosphere. The obtained mixture was stirred at room temperature for 30 minutes. To this mixture was added 4.5 ml of methanol, and stirring was performed at room temperature for 30 minutes. The obtained reaction mixture was added with ice-cooling to 325 ml of 2 N hydrochloric acid, and extraction was performed with ethyl acetate. The ethyl acetate layer was washed with saturated brine, dried over sodium sulfate, and then filtered, and the filtrate was concentrated. The obtained residue was purified by silica gel column chromatography (ethyl acetate:methanol=100:0→93:7). The purified product was concentrated under reduced pressure to give 10.5 g of white amorphous solid target compound.

Yield: 91%

$^1$H-NMR (Toluene-$d_8$, 100° C.) δ ppm: 1.5-2.0 (4H, m), 2.41 (3H, s), 2.49 (3H, s), 3.0-4.2 (2H, m), 5.5 (0.5H, d, J=4.8 Hz), 5.5-5.8 (1H, m), 6.6 (1H, d, J=8.3 Hz), 6.7-6.9 (1H, m), 6.9-7.2 (6H, m), 7.3-7.5 (2H, m), 7.81, 7.84 (0.5H, d, J=8.1 Hz)

Example 18

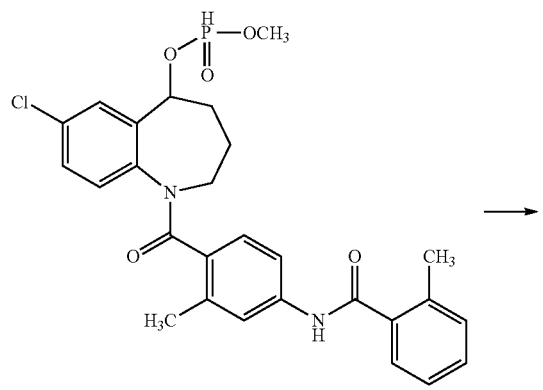

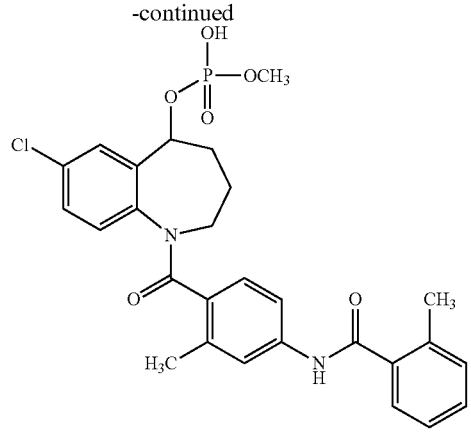

A 0.1 ml quantity of water and 254 mg (1.0 mmol) of iodine were added to a pyridine solution (5 ml) of 500 mg (0.95 mmol) of the compound of Example 17, and the obtained mixture was stirred at room temperature for 30 minutes. To this mixture was added 2 ml of triethylamine, and concentration under reduced pressure was performed. A 20 ml quantity of toluene was added to the residue, and concentration under reduced pressure was performed. Water was added to the residue, and washing was performed with a mixed solvent of ethyl acetate and diethyl ether. To the aqueous layer was added 1 N hydrochloric acid, and extraction was performed with ethyl acetate. The ethyl acetate layer was dried over sodium sulfate and then filtered, and the filtrate was concentrated. The obtained residue was purified by silica gel column chromatography (dichloromethane:methanol=90:10→50:50). The purified product was concentrated under reduced pressure, and the residue was dissolved in 30 ml of water. The obtained solution was filtered through celite, and the filtrate was freeze-dried to give 140 mg of white amorphous solid target compound.

$^1$H-NMR (Toluene-$d_8$, 100° C.) δ ppm: 1.4-2.0 (4H, m), 2.33 (3H, s), 2.34 (3H, s), 2.5-4.5 (5H, m), 5.4-5.7 (2H, m), 6.5 (2H, d, J=7.9 Hz), 6.7 (2H, d, J=7.9 Hz), 6.8-7.2 (5H, m), 7.2-7.4 (2H, m), 7.55 (1H, s)

Example 19

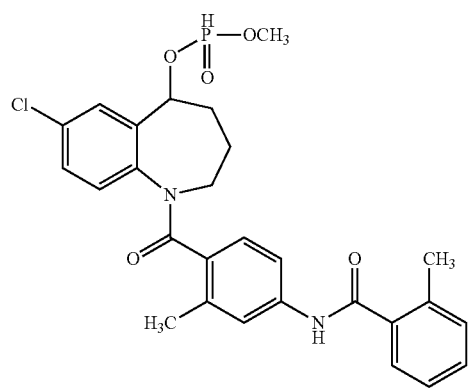

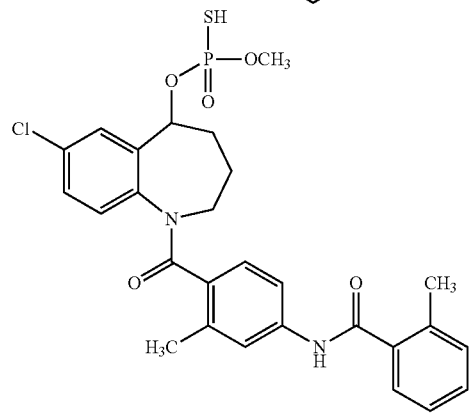

A 64 mg quantity (1.0 mmol) of sulfur was added to a pyridine solution (5 ml) of 500 mg (0.9 mmol) of the compound of Example 17, and the obtained mixture was stirred at room temperature for 2 hours. To this mixture was added 1 ml of triethylamine, and concentration under reduced pressure was performed. A 10 ml quantity of toluene was added to the obtained residue, and concentration under reduced pressure was performed. Water was added to the residue for dissolution, and filtration was performed using celite. To the filtrate was added 1 N hydrochloric acid, and extraction was performed with ethyl acetate. The ethyl acetate layer was dried over sodium sulfate and then filtered, and the filtrate was concentrated. Water was added to the obtained residue, and the insoluble matter was collected by filtration and then dried to give 300 mg of white powdery target compound.

$^1$H-NMR (Toluene-d$_8$, 100° C.) δ ppm: 1.1-2.0 (4H, m), 2.2-2.5 (6H, m), 3.5 (3H, dd, J=13.9, 14.9 Hz), 2.5-5.0 (2H, m), 3.5-5.7 (1H, m), 6.4-7.5 (10H, m)

Example 20

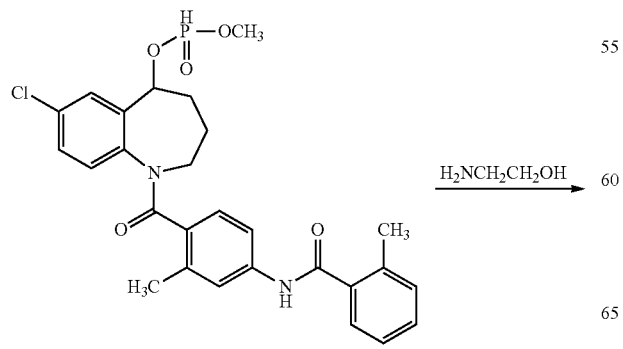

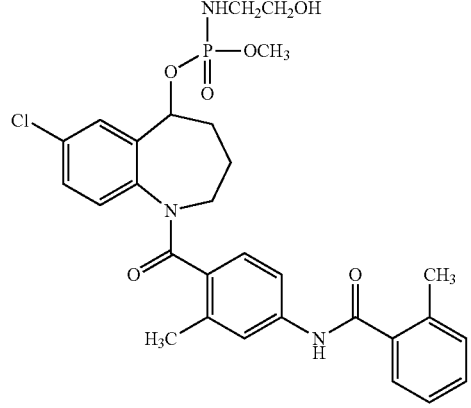

A 0.5 ml quantity of water, 0.5 ml of carbon tetrachloride, 0.5 ml of triethylamine, and 0.072 ml (1.2 mmol) of ethanolamine were added to an acetonitrile solution (5 ml) of 500 mg (0.95 mmol) of the compound of Example 17, and the obtained mixture was stirred at room temperature for 10 minutes. Water was added to this mixture, and extraction was performed with ethyl acetate. The ethyl acetate layer was washed with saturated brine, dried over sodium sulfate, and then filtered, and the filtrate was concentrated. The obtained residue was purified by silica gel column chromatography (ethyl acetate:methanol=100:0→80:20). The purified product was concentrated under reduced pressure to give 540 mg of white amorphous solid target compound.

$^1$H-NMR (DMSO-d$_6$, 100° C.) δ ppm: 1.6-2.3 (4H, m), 2.36 (6H, s), 2.7-3.1 (2H, m), 2.5-4.5 (2H, m), 3.3-3.5 (2H, m), 3.65 (3H, dd, J=9.6, 11.2 Hz), 4.0-4.3 (1H, m), 4.4-4.8 (1H, m), 5.3-5.7 (1H, m), 6.7-7.1 (2H, m), 7.1-7.5 (5H, m), 7.57 (1H, s), 9.76 (1H, s)

Example 21

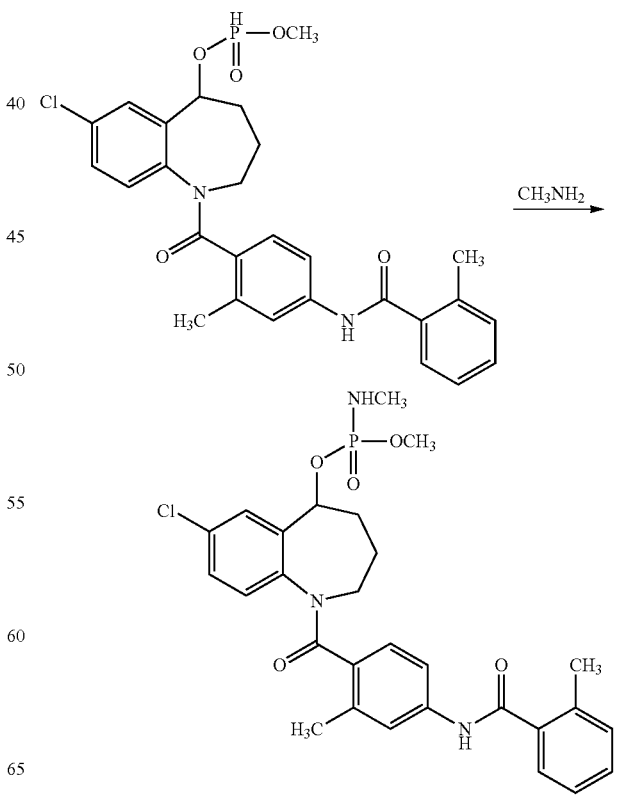

A 0.5 ml quantity of water, 0.5 ml of carbon tetrachloride, 0.5 ml of triethylamine, and 0.119 ml (1.2 mmol) of methylamine (40% methanol solution) were added to an acetonitrile solution (5 ml) of 500 mg (0.95 mmol) of the compound of Example 17, and the obtained mixture was stirred at room temperature for 10 minutes. Water was added to this mixture, and extraction was performed with ethyl acetate. The ethyl acetate layer was washed with saturated brine, dried over sodium sulfate, and then filtered, and the filtrate was concentrated. The obtained residue was purified by silica gel column chromatography (ethyl acetate:methanol=94:6→85:15). The purified product was concentrated under reduced pressure to give 250 mg of white amorphous solid target compound.

$^1$H-NMR (DMSO-d$_6$, 100° C.) δ ppm: 1.7-2.3 (4H, m), 2.37 (6H, s), 2.4-2.6 (3H, m), 2.8-4.3 (2H, m), 3.63 (3H, t, J=10.7 Hz), 4.4-4.8 (1H, m), 5.3-5.6 (1H, m), 6.6-7.1 (2H, m), 7.1-7.5 (5H, m), 7.58 (1H, s), 9.81 (1H, s)

Example 22

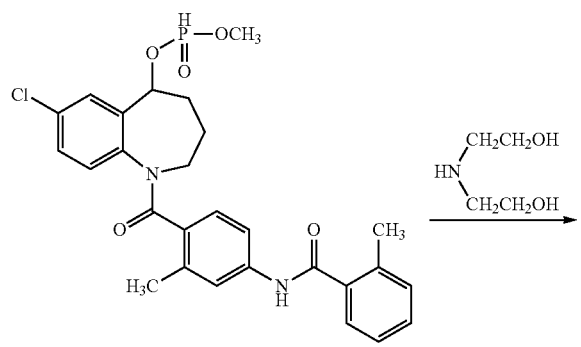

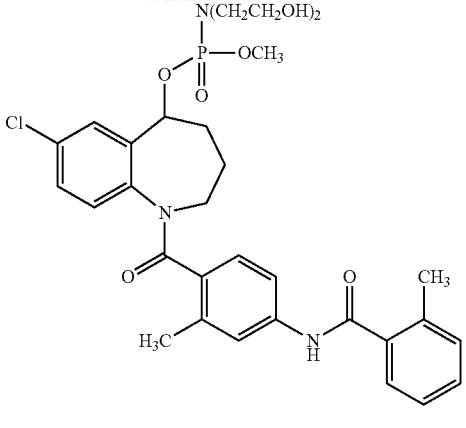

A 0.5 ml quantity of water, 0.5 ml of carbon tetrachloride, 0.5 ml of triethylamine, and 0.115 ml (1.2 mmol) of diethanolamine were added to an acetonitrile solution (5 ml) of 500 mg (0.95 mmol) of the compound of Example 17, and the obtained mixture was stirred at room temperature for 10 minutes. Water was added to this mixture, and extraction was performed with ethyl acetate. The ethyl acetate layer was washed with saturated brine, dried over sodium sulfate, and then filtered, and the filtrate was concentrated. The obtained residue was purified by silica gel column chromatography (ethyl acetate:methanol=88:12→70:30). The purified product was concentrated under reduced pressure, and the residue was recrystallized from water-containing methanol to give 250 mg of white powdery target compound.

$^1$H-NMR (DMSO-d$_6$, 100° C.) δ ppm: 1.6-2.2 (4H, m), 2.37 (6H, s), 3.0-3.2 (4H, m), 3.5-3.7 (7H, m), 2.8-4.3 (2H, m), 4.1-4.4 (1H, m), 5.3-5.7 (1H, m), 6.7-7.1 (2H, m), 7.1-7.5 (7H, m), 7.5-7.7 (1H, m), 9.80 (1H, br)

Example 23

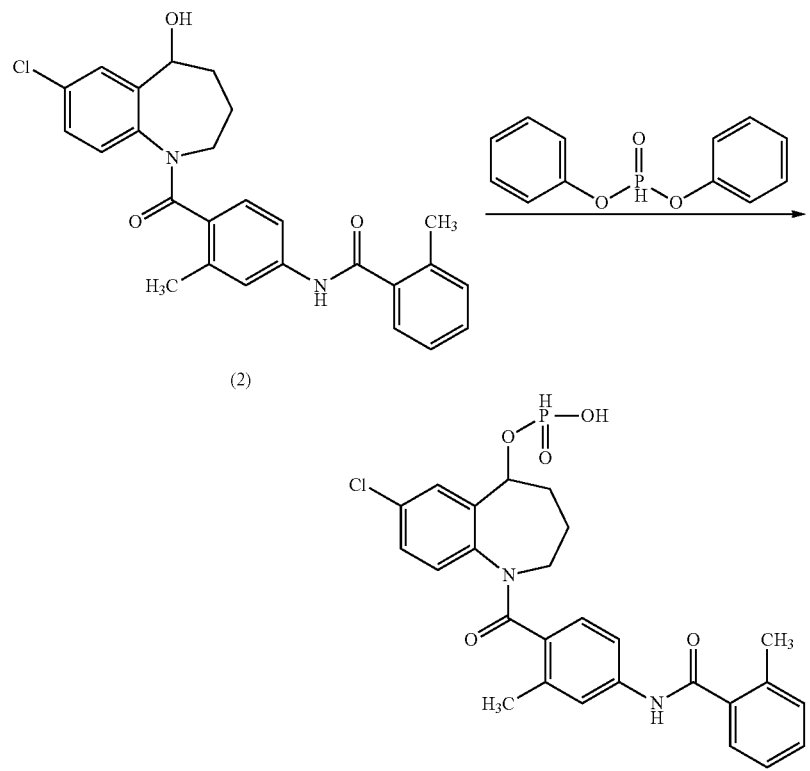

(2)

A 3.8 mg (20 mmol) quantity of diphenyl phosphite was added to a pyridine solution (10 ml) of 3.0 g (6.7 mmol) of tolvaptan (compound (2)), and the obtained mixture was stirred at room temperature for 1 hour. To this mixture was added 2 ml of water, and stirring was performed at room temperature for 30 minutes. The obtained reaction mixture was concentrated under reduced pressure, 1 N hydrochloric acid was added to the residue, and extraction was performed with ethyl acetate. The ethyl acetate layer was washed with saturated brine twice, dried over sodium sulfate, and then filtered, and the filtrate was concentrated. The obtained residue was purified by silica gel column chromatography (ethyl acetate:methanol=100:0→50:50). The purified product was concentrated under reduced pressure. The residue was dissolved in water, and the insoluble matter precipitated by adding 1 N hydrochloric acid was collected by filtration and then dried to give 0.83 g of white powdery target compound.

Yield: 24%

$^1$H-NMR (DMSO-d$_6$, 100° C.) δ ppm: 1.7-2.2 (4H, m), 2.35 (3H, s), 2.36 (3H, s), 2.8-4.3 (2H, m), 5.4-5.6 (1H, m), 5.8 (0.5H, br), 6.7-7.4 (8H, m), 7.47 (1H, d, J=2.3 Hz), 7.55 (1H, s), 9.79 (1H, br)

Example 24

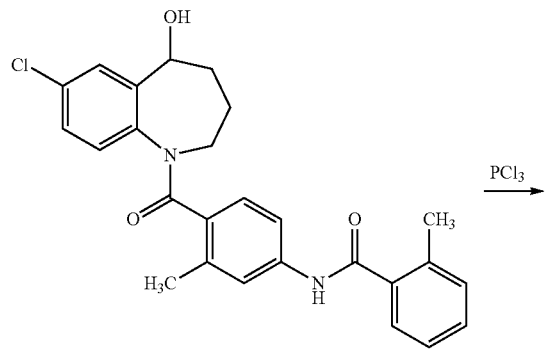

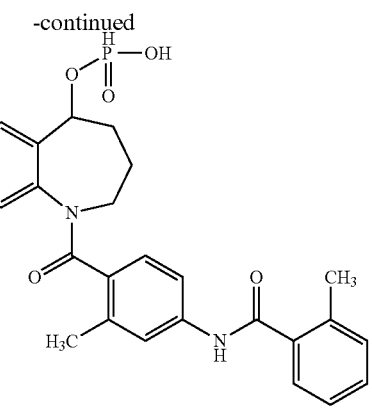

A 2.9 ml quantity of phosphorus trichloride was added under a nitrogen stream to tetrahydrofuran (THF) (29 ml). The obtained mixture was ice-cooled, and 6.1 ml (44 mmol) of triethylamine was added thereto. This mixture was cooled in an ice-methanol bath. A THF solution (120 ml) of 10.0 g (22 mmol) of tolvaptan (compound (2)) was then added dropwise thereto at an internal temperature of not more than −10° C., and stirring was performed at the same temperature for 2 hours. A 130 ml quantity of 1 N sodium hydroxide aqueous solution was added dropwise to the obtained reaction mixture at an internal temperature of not more than 0° C., 200 ml quantity of water was further added thereto, and washing was performed with toluene twice. The obtained aqueous solution was cooled in an ice-methanol bath, 1 N HCl was added dropwise thereto at an internal temperature of not more than 0° C., and extraction was performed with ethyl acetate. The ethyl acetate layer was dried over sodium sulfate and then filtered, and the filtrate was concentrated to give 6.8 g of white amorphous solid target compound.

Yield: 60%

Example 25

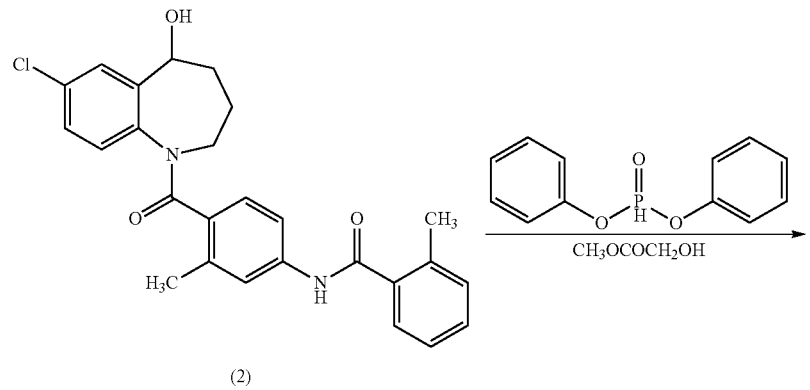

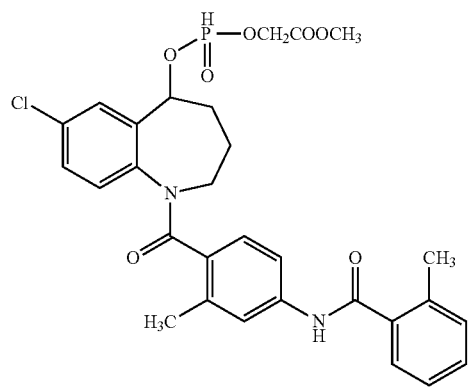

quantity of 3.8 ml (20 mmol) of diphenyl phosphite was added to a pyridine solution (10 ml) of 3.0 g (6.7 mmol) of tolvaptan (compound (2)), and the obtained mixture was stirred at room temperature for 1 hour. To this mixture was added 5.2 ml (66.6 mmol) of methyl glycolate, and stirring was performed at room temperature for 12 hours. To the reaction mixture was added 50 ml of water, and extraction was performed with ethyl acetate. The ethyl acetate layer was washed with 1 N hydrochloric acid twice, dried over sodium sulfate, and then filtered, and the filtrate was concentrated. The obtained residue was purified by silica gel column chromatography (n-hexane:ethyl acetate=50:50→0:100). The purified product was concentrated under reduced pressure to give 0.79 g of white amorphous solid target compound.

Yield: 20%

$^1$H-NMR (Toluene-$d_8$, 100° C.) δ ppm: 1.6-2.2 (4H, m), 2.51 (3H, s), 2.60 (3H, s), 3.2-4.4 (2H, m), 3.53 (3H, s), 4.43 (1H, s), 4.47 (1H, s), 5.87 (0.5H, s), 5.9-6.1 (1H, m), 6.6-6.8 (1H, m), 6.8-7.0 (2H, m), 7.0-7.4 (5H, m), 7.48 (1H, s), 7.63 (1H, s), 8.27 (0.5H, s).

Example 26

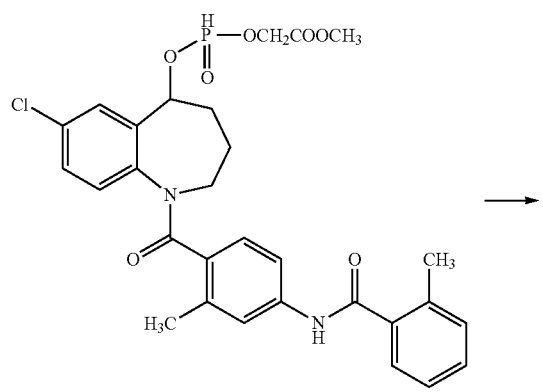

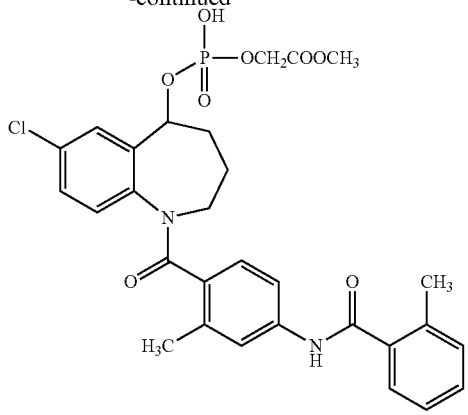

A 0.8 ml quantity of water was added to a pyridine solution (7.9 ml) of 0.79 g (1.35 mmol) of the compound of Example 25. To the obtained mixture was added with ice-cooling 0.34 g (2.7 mmol) of iodine, and stirring was performed at room temperature for 1 hour. To the reaction mixture was added 1 N hydrochloric acid, and extraction was performed with ethyl acetate. The ethyl acetate layer was washed with saturated brine, dried over sodium sulfate, and then filtered, and the filtrate was concentrated. The obtained residue was dissolved in water and then freeze-dried to give 80 mg of white amorphous solid target compound.

Yield: 9.9%

$^1$H-NMR (DMSO-$d_6$, 100° C.) δ ppm: 1.7-2.3 (4H, m), 2.35 (3H, s), 2.36 (3H, s), 2.8-4.3 (2H, m), 4.49 (2H, dd, J=1.7, 10.1 Hz), 5.4-5.6 (1H, m), 6.7-7.1 (2H, m), 7.1-7.5 (7H, m), 7.54 (1H, s), 9.79 (1H, br)

Example 27

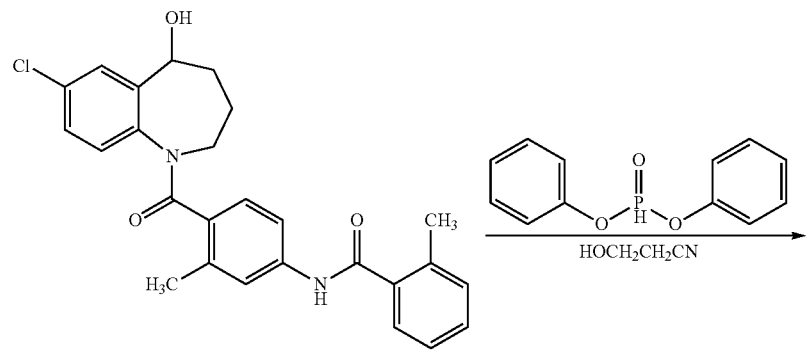

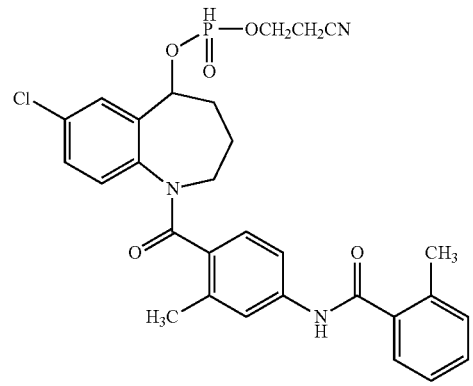

A 3.0 g quantity (6.7 mmol) of tolvaptan (compound (2)) were added in small portions to a pyridine solution (15 ml) of 3.8 ml (20 mmol) of diphenyl phosphite, and the obtained mixture was stirred at room temperature for 0.5 hours. To this mixture was added 2.8 ml (40 mmol) of 3-hydroxypropionitrile, and stirring was performed at room temperature for 0.5 hours. To the obtained reaction mixture was added 1 N hydrochloric acid, and extraction was performed with ethyl acetate. The ethyl acetate layer was washed with water, dried over sodium sulfate, and then filtered, and the filtrate was concentrated. The obtained residue was purified by silica gel column chromatography (ethyl acetate:methanol=100:0→10:1). The purified product was concentrated under reduced pressure to give 2.8 g of white amorphous solid target compound.

Yield: 75%

$^1$H-NMR (Toluene-d$_8$, 100° C.) δ ppm: 1.4-2.0 (6H, m), 2.33 (3H, s), 2.40 (3H, s), 3.1-3.8 (4H, m), 5.40 (0.5H, d, J=3.1 Hz), 5.3-5.4 (1H, m), 6.5-6.7 (1H, m), 6.7-6.9 (1H, m), 6.9-7.2 (6H, m), 7.2-7.5 (2H, m), 7.76 (0.5H, d, J=8.5 Hz)

added 1 N hydrochloric acid, and extraction was performed with ethyl acetate. The ethyl acetate layer was dried over sodium sulfate and then filtered, and the filtrate was concentrated. The obtained residue was purified by silica gel column chromatography (ethyl acetate:methanol=100:0→85:15). The purified product was concentrated under reduced pressure to give 0.91 g of white amorphous solid target compound:

Yield: 85%

$^1$H-NMR (DMSO-d$_6$, 100° C.) δ ppm: 1.6-1.9 (3H, m), 2.0-2.3 (1H, m), 2.10 (3H, m), 2.36 (6H, s), 2.3-4.2 (2H, m), 2.7-2.8 (2H, m), 3.9-4.2 (2H, m), 5.5-5.8 (1H, m), 6.7-6.9 (1H, m), 7.0-7.4 (7H, m), 7.4-7.5 (1H, m), 7.56 (1H, s), 7.7-7.8 (0.3H, m), 8.5-8.6 (m, 0.7H), 9.76 (1H, br)

Example 29

Example 28

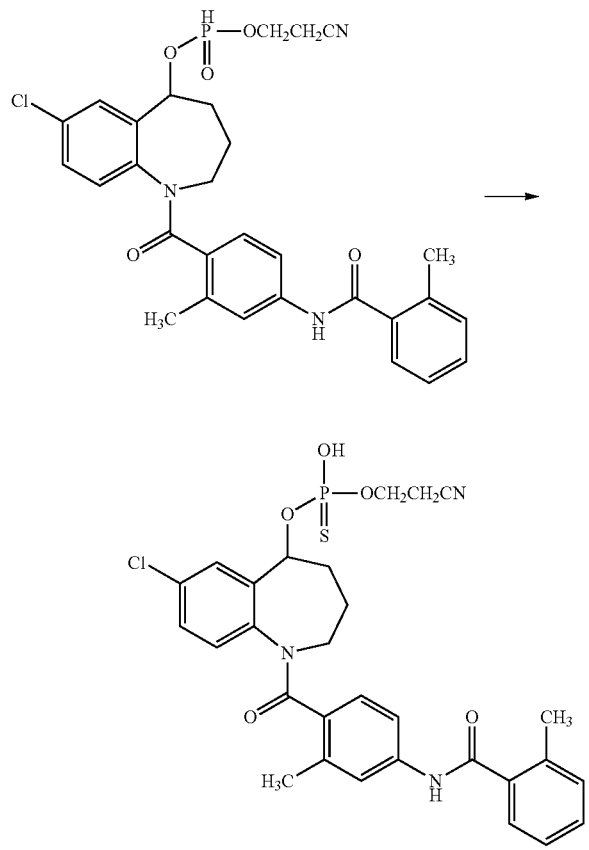

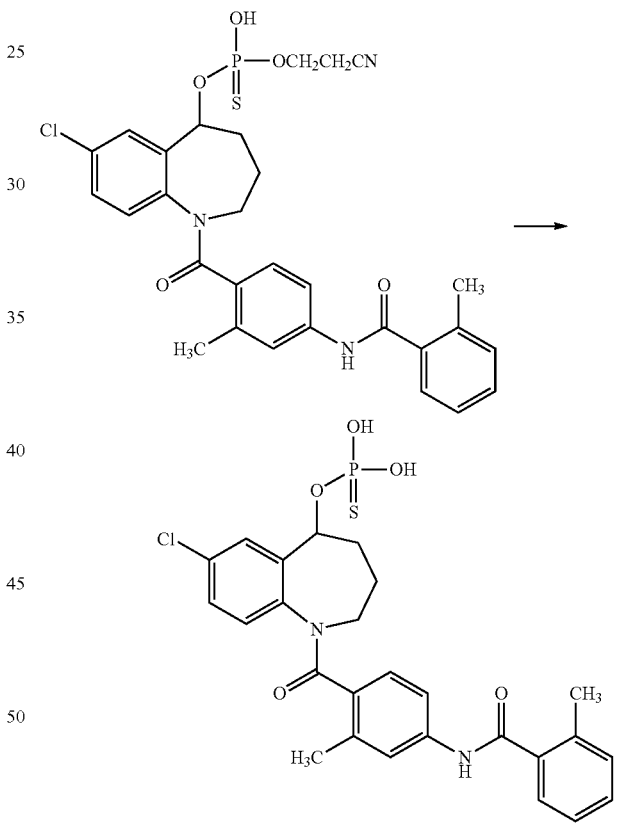

A 300 mg quantity (0.5 mmol) of the compound of Example 28 was added to 5 ml of 28% aqueous ammonia, and the obtained mixture was stirred at room temperature for three days. To this mixture was added 1 N hydrochloric acid. The precipitated solids were collected by filtration and then dried to give 100 mg of white powdery target compound.

Yield: 37%

$^1$H-NMR (Pyridine-d$_5$-D$_2$O, 90° C.) δ ppm: 1.6-2.4 (4H, m), 2.43 (3H, s), 2.53 (3H, s), 2.8-4.3 (2H, m), 5.1-5.4 (1H, m), 6.8-7.3 (6H, m), 7.4-7.7 (2H, m), 7.7-8.1 (2H, m)

A 0.115 g quantity (3.6 mmol) of sulfur was added to a pyridine solution (10 ml) of 1.0 g (1.8 mmol) of the compound of Example 27, and the obtained mixture was stirred at room temperature for 2 hours. To this mixture was

Example 30

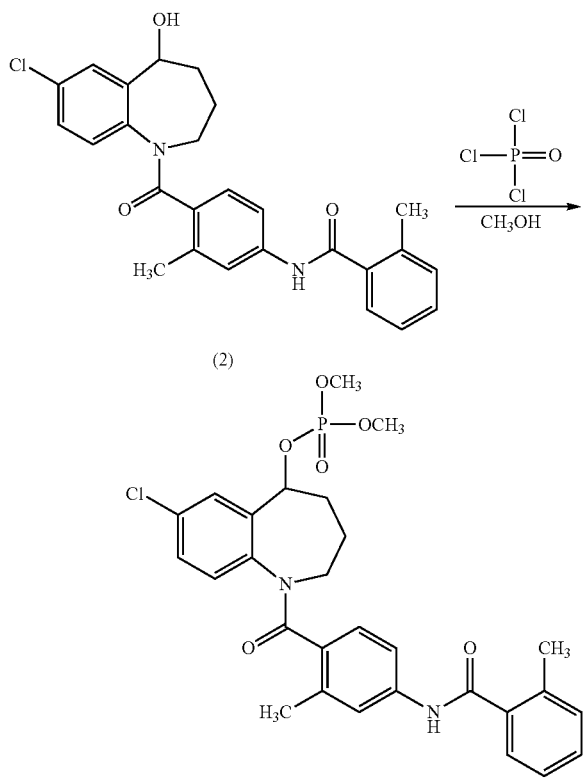

A 0.62 ml quantity (6.6 mmol) of phosphorus oxychloride and 0.92 ml (6.6 mmol) of triethylamine were added under a nitrogen stream to tetrahydrofuran (THF) (5 ml). The obtained mixture was cooled in an ice-methanol bath. A THF solution (10 ml) of 1.0 g (2.2 mmol) of tolvaptan (compound (2)) was then added dropwise thereto, and stirring was performed at the same temperature for 30 minutes. To this mixture were added 2.8 ml (20 mmol) of triethylamine and 1.1 ml (26.4 mmol) of methanol, and stirring was performed for 30 minutes. Water was added to the obtained reaction mixture, and extraction was performed with ethyl acetate. The ethyl acetate layer was dried over sodium sulfate and then filtered, and the filtrate was concentrated. The obtained residue was purified by silica gel column chromatography (ethyl acetate:methanol=100:0→80:20). The purified product was concentrated under reduced pressure, and the residue was recrystallized from water-containing methanol to give 400 mg of white powdery target compound.

Yield: 33%

$^1$H-NMR (DMSO-d$_6$, 100° C.) δ ppm: 1.7-2.2 (4H, m), 2.36 (6H, s), 2.8-4.3 (2H, m), 3.71 (6H, dd, J=10.2, 11.1 Hz), 5.5-5.6 (1H, m), 6.8-7.1 (2H, m), 7.1-7.5 (7H, m), 7.58 (1H, s), 9.80 (1H, br)

Test Example 1

Solubility of Compound (1b)

Compound (1b) as obtained in Example 3 or 4 was added in excess to 0.1 N sodium phosphate buffer (pH 5, pH 6, pH 7, pH 8, pH 9, or pH 10), 0.1 N Tris/HCl buffer (pH 8 or pH 9), 0.1 N sodium hydrogencarbonate/HCl buffer (pH 8) or 0.1 N sodium citrate buffer (pH 8), and then shaken at room temperature for 16 days. If the test compound dissolved even after about 6 to about 8 w/v % had been added thereto, no further test compound was added.

Each solution was filtered through a 0.45-μm filter, and then, under the following HPLC conditions, the solubility of compound (1b) was determined by absolute calibration.

HPLC Conditions

Detection: ultraviolet absorption photometer
  (measurement wavelength: 254 nm)
Column: YMC(ODS) AM-302 (4.6×150 mm)
Column temperature: constant temperature of approximately 2'5° C.
Eluate: acetonitrile/water/phosphoric acid=450/550/1
Flow rate: 1 ml/min
Injection volume: 10 μl

TABLE 1

Solubility of compound (1b) in buffer solution (room temperature)

| Solvent (100 mM buffer) | pH before dissolution | pH after dissolution | Solubility of compound (1b) (w/v %) |
|---|---|---|---|
| Sodium phosphate buffer | 5 | 3.0 | 0.58 |
|  | 6 | 3.0 | 1.31 |
|  | 7 | 3.1 | 0.76 |
|  | 8 | 3.3 | at least 7.1* |
|  | 9 | 3.3 | at least 7.4* |
|  | 10 | 3.4 | at least 6.5* |
| Tris buffer | 8 | 2.9 | 0.74 |
|  | 9 | 3.4 | at least 6.3* |
| Citric acid buffer | 8 | 4.2 | at least 8.3* |
| Sodium hydrogencarbonate buffer | 8 | 3.1 | at least 7.1* |

*Sample having a solubility so high that crystals could not be added in excess

Test Example 2

Solubility of Salt of Compound (1)

A suitable amount of test compound is added to a test tube, and 2.5 ml of water is added thereto. After shaking at 37° C. for 30 minutes, the mixture is filtered through a 0.45-μm membrane filter, and 0.5 ml of the filtrate is accurately weighed. Mobile phase is added thereto to make exactly 50 ml, preparing a test solution (dilution ratio: 100-fold). Approximately 5 mg of free-form authentic sample is accurately weighed, and acetonitrile is added thereto to make exactly 50 ml. A 2 ml of this liquid is accurately weighed, and mobile phase is added thereto to make exactly 20 ml, preparing a standard solution (equivalent to 10 μg/ml). By liquid chromatography under the following conditions, 20 μl of both the test solution and standard solution are tested to obtain the peak areas At and As of the test solution and standard solution.

$$\text{Concentration}(\mu g/ml) = Ws \times 5 \times 10 \times At/As \times 100 = Ws \times At/As \times 200$$

Ws: weighed amount of authentic sample (mg)

Test Conditions

Detection: ultraviolet absorption photometer
  (measurement wavelength: 254 nm)
Column: TOSOH TSKgel ODS-80Ts (0.46 cm×15 cm)
Column temperature: constant temperature of approximately 40° C.
Mobile phase: water/acetonitrile/trifluoroacetic acid=500/500/1
Flow rate: 1 ml/min

TABLE 2

| Test compound (Example No.) | Solubility (w/v %) |
| --- | --- |
| 5 | >0.1 |
| 7 | >0.1 |
| 8 | >0.1 |
| 11 | >0.1 |
| 16 | >0.1 |
| 17 | >0.1 |
| 20 | >0.1 |
| 31 | >0.1 |

Test Example 3

Solubility of Tolvaptan

Tolvaptan was added in excess to Britton-Robinson buffer (pH 2, pH 7, or pH 12) or purified water, and then shaken at 25° C.±1° C. for 4 hours. Each solution was filtered through a filter, and then, using HPLC, the solubility of tolvaptan was quantified by absolute calibration.

TABLE 3

Solubility of tolvaptan in Britton-Robinson buffer and purified water

| Solvent | Solubility of tolvaptan (w/v %) |
| --- | --- |
| Water | 0.00002 |
| pH 2 | 0.00002 |
| pH 7 | 0.00003 |
| pH 12 | 0.00002 |

Test Example 4

Serum Concentration of Tolvaptan in Female Rats after Tail-Vein Administration of a Compound (1b) Solution Experiment Method A solution of compound (1b) (equivalent to 1 mg of tolvaptan per ml of solution) was prepared.

TABLE 4

Formulation (in 1 ml)

| | Amount (mg) |
| --- | --- |
| Compound (1b) | 1.0* |
| Sodium dihydrogenphosphate•dihydrate | 0.79 |
| Mannitol | 50 |
| Sodium hydroxide | Suitable amount to adjust to pH 7.0 |
| Water for Injection | Suitable amount |

*Amount equivalent to 1.0 mg of tolvaptan per ml of solution

Preparation Method

A 79 mg quantity of sodium dihydrogenphosphate•dihydrate and 5 g of mannitol were dissolved in about 90 ml of water for injection. A sodium hydroxide solution was added thereto, and a solution of pH 7 was prepared. Compound (1b) equivalent to 100 mg of tolvaptan was dissolved in this solution. A sodium hydroxide solution was added thereto, and the pH was adjusted to 7. Injection solvent was added to the obtained solution to make 100 ml, and sterile filtration was performed with a 0.2-μm filter to prepare a solution of compound (1b) (equivalent to 1 mg of tolvaptan per ml of solution).

This solution was rapidly administered to female rats via the tail vein at a dose such that 1 mg of tolvaptan is produced per kg of body weight. From time to time, blood was collected from the jugular vein under light ethyl ether anesthesia, and serum concentration of tolvaptan was determined by high-speed liquid chromatography (HPLC).

The results are shown in FIG. 1.

Tolvaptan was initially detected five minutes after the intravenous administration of a solution of compound (1b) to female rats. This indicates that compound (1b) is rapidly hydrolyzed into tolvaptan in rats.

Test Example 5

Serum Concentration of Tolvaptan in Female Rats after Oral Administration of a Compound (1b) Solution Experiment Method A solution of compound (1b) (equivalent to 0.4 mg of tolvaptan per ml of solution) was prepared.

TABLE 5

Formulation (in 1 ml)

| | Amount (mg) |
| --- | --- |
| Compound (1b) | 0.4* |
| Sodium hydrogencarbonate | 2 |
| Sodium hydroxide | Suitable amount (pH 9.1) |
| Water for Injection | Suitable amount |

*Amount equivalent to 0.4 mg of tolvaptan per ml of solution

Preparation Method

A 1 g quantity of sodium hydrogencarbonate was dissolved in about 400 ml of water for injection. A sodium hydroxide solution was added thereto to adjust the pH to 9.0, and water for injection was added thereto, preparing 500 ml of 0.2% sodium hydrogencarbonate solution. An 89 μl quantity of 1 N sodium hydroxide solution and compound (1b) equivalent to 20 mg of tolvaptan were added to about 40 ml of this 0.2% sodium hydrogencarbonate solution and dissolved. A 0.2% sodium hydrogencarbonate solution was further added thereto to make 50 ml, thereby preparing a solution of compound (1b) (equivalent to 0.4 mg of tolvaptan per ml of solution). The pH of this solution was 9.1. This solution is called "Solution A" hereinafter.

A spray-dried tolvaptan powder equivalent to 60 mg of tolvaptan, which was prepared in a similar manner to Example 3 of JP1999-21241-A, was suspended in 50 ml of water for injection in a porcelain mortar. This suspension was diluted three-fold with water for injection, preparing a suspension of spray-dried powder equivalent to 0.4 mg of tolvaptan per ml of suspension. This suspension is called "Suspension B" hereinafter.

The following tests were performed in order to examine the oral absorption characteristics of Solution A and Suspension B. Wistar female rats (body weight about 160 g) which had been fasted for about 18 hours were used as test animals. Solution A and Suspension B were each administered by forced oral administration using a sonde for oral administration at a dose of 2.5 ml/kg of body weight, producing 1 mg of tolvaptan per kg of body weight. The blood samples were collected from the jugular vein under light ethyl ether anesthesia periodically after dosing, and the serum concentrations of tolvaptan were determined by using HPLC-MS/MS (Waters).

Figure 2:
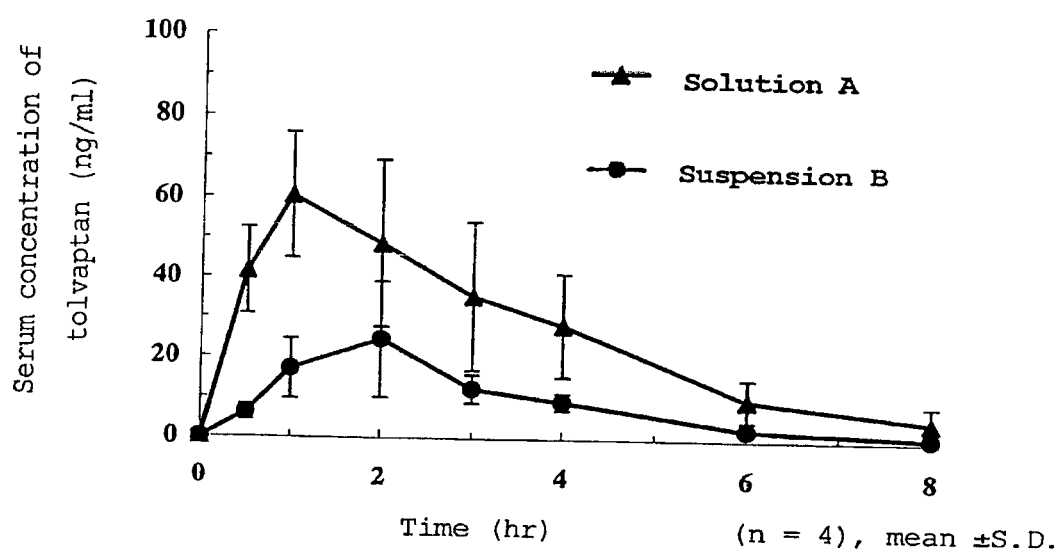
FIG. 2 is a graph showing the change in serum concentration of tolvaptan in female rats after oral administration of a solution of compound (1b) at a dose such that 1 mg of tolvaptan is produced per kg of body weight.

The obtained results are shown in FIG. 2 and Table 6. FIG. 2 shows the serum concentration-time profiles of tolvaptan after an oral administration of Solution A and suspension B (n=4). Table 6 shows the mean of the pharmacokinetic parameter values (n=4). The parameters in Table 6 have the following meanings.

$AUC_{8hr}$: area under the serum concentration-time curve for up to 8 hours after administration (ng·hr/ml)
$AUC_\infty$: area under the serum concentration-time curve for up to an infinite time after administration (ng·hr/ml)
$C_{max}$: maximum serum concentration (ng/ml)
$T_{max}$: time to reach the maximum serum concentration (hr)

As a result, it was confirmed that that the solution of compound (1b) (Solution A) takes a shorter time to reach the maximum serum concentration than the suspension of spray-dried tolvaptan (Suspension B), and also leads to greater maximum serum concentration ($C_{max}$) and larger areas under the serum concentration-time curve ($AUC_{8hr}$, $AUC_\infty$).

TABLE 6

|  | $AUC_{8\,hr}$ (ng · hr/mL) | $C_{max}$ (ng/mL) | $T_{max}$ (hr) | $AUC_\infty$ (ng · hr/mL) |
| --- | --- | --- | --- | --- |
| Solution A | 217.5 | 61.0 | 1.3 | 230.1 |
| Suspension B | 73.2 | 26.4 | 1.5 | 76.1 |

These results revealed that when administered in vivo, the compound of the present invention, compound (1b) in particular, increases absorption even more than conventional absorption improvement by amorphization, and consequently improves bioavailability of tolvaptan.

Preparation Example 1

A 79 mg quantity of sodium dihydrogenphosphate·dihydrate and 5 g of mannitol were dissolved in about 90 ml of injection solvent. A sodium hydroxide solution was added thereto, preparing a solution of pH 7. Compound (1b) equivalent to 100 mg of tolvaptan was added to this solution. A sodium hydroxide solution was added thereto, adjusting the pH to 7. Injection solvent was added to the obtained solution to make 100 ml, and sterile filtration was performed using a 0.2-μm filter to give an injection of the present invention containing compound (1b) (equivalent to 1 mg of tolvaptan per ml of injection).

Preparation Example 2

A 79 mg of sodium dihydrogenphosphate·dihydrate and 5 g mannitol were dissolved in about 90 ml of injection solvent. A sodium hydroxide solution was added thereto, preparing a solution pH of 7.5. Compound (1b) equivalent to 10 mg of tolvaptan was dissolved in the solution. Injection solvent was added to the obtained solution to make 100 ml, and sterile filtration was performed with a 0.2-μm filter to prepare an injection of the present invention containing compound (1b) (equivalent to 0.1 mg tolvaptan per ml of injection).

Preparation Example 3

A 380 mg quantity of trisodium phosphate·dodecahydrate and g of mannitol were dissolved in about 90 ml of injection solvent. Compound (1b) equivalent to 100 mg, 300 mg or 1000 mg of tolvaptan was dissolved in the obtained solution. When dissolving compound (1b) equivalent to 1000 mg of tolvaptan, a sodium hydroxide solution was added to improve the solubility. The pH of each obtained solution was adjusted to 8 to 9 with sodium hydroxide or hydrochloric acid, and an injection solvent was added thereto to make 100 ml. The obtained solution was sterile-filtered through a 0.2-μm filter, preparing injections of the present invention containing compound (1b) (equivalent to 1 mg, 3 mg or 10 mg of tolvaptan per ml of injection).

The invention claimed is:

1. A benzoazepine compound represented by formula (1)

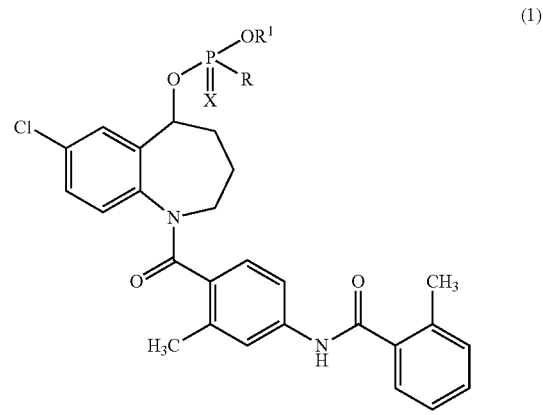

or a salt thereof,
wherein R represents a hydrogen atom, a hydroxy group optionally protected with a protecting group, a mercapto group optionally protected with a protecting group, or an amino group optionally protected with one or two protecting groups; $R^1$ represents a hydrogen atom or a hydroxy-protecting group; and X represents an oxygen atom or a sulfur atom.

2. A benzoazepine compound according to claim 1 or a salt thereof, wherein X is an oxygen atom.

3. A benzoazepine compound according to claim 1 or 2, or a salt thereof, wherein R is a hydroxy group optionally protected with a protecting group.

4. A benzoazepine compound according to claim 1 or 2, or a salt thereof, wherein R is a hydrogen atom, a mercapto group optionally protected with a protecting group, or an amino group optionally protected with one or two protecting groups.

5. A benzoazepine compound according to any one of claims 1, 2, 3 and 4, or a salt thereof, wherein $R^1$ is a hydroxy-protecting group.

6. A benzoazepine compound according to any one of claims 1, 2, 3 and 4, or a salt thereof, wherein $R^1$ is a hydrogen atom.

7. A benzoazepine compound according to claim 1 or a salt thereof, wherein X is a sulfur atom.

8. A benzoazepine compound according to claim 1 or a salt thereof, wherein X is an oxygen atom, R is a hydroxy group, and $R^1$ is a hydrogen atom.

9. A pharmaceutical composition comprising a benzoazepine compound of claim 1 or a pharmaceutically acceptable salt thereof, together with a pharmaceutically acceptable diluent and/or carrier.

10. A pharmaceutical composition according to claim 9, for use as a vasodilator, hypotensor, aquaretic agent, PKD, or platelet aggregation inhibitor.

11. An aqueous solution composition comprising a benzoazepine compound of claim 1 or a pharmaceutically acceptable salt thereof.

12. An aqueous solution composition according to claim 11, comprising a benzoazepine compound of claim 1 or a pharmaceutically acceptable salt thereof, together with a buffer, isotonizing agent and injection solvent, and which is in the form of an injection.

13. An aqueous solution composition according to claim 12, further comprising a pH adjuster.

* * * * *